(12) United States Patent
Oko et al.

(10) Patent No.: US 11,854,690 B2
(45) Date of Patent: Dec. 26, 2023

(54) SYSTEMS AND METHODS FOR AN UNIVERSAL INDEXING SCHEME FOR INDEXING DATA

(71) Applicant: Innovative Perioperative Technologies, LLC, Southbury, CT (US)

(72) Inventors: Walter J. Oko, Woodbridge, CT (US); Wojciech Wojenski, Hamden, CT (US); David Nichols, Southbury, CT (US)

(73) Assignee: Innovative Perioperative Technologies, LLC, Portsmouth, NH (US)

( * ) Notice: Subject to any disclaimer, the term of this patent is extended or adjusted under 35 U.S.C. 154(b) by 237 days.

(21) Appl. No.: 17/146,251

(22) Filed: Jan. 11, 2021

(65) Prior Publication Data
US 2022/0223263 A1 Jul. 14, 2022

(51) Int. Cl.
| | | |
|---|---|---|
| *G06F 16/16* | (2019.01) | |
| *G16H 40/20* | (2018.01) | |
| *G06N 5/04* | (2023.01) | |
| *G16H 70/20* | (2018.01) | |
| *G16H 50/70* | (2018.01) | |
| *G06F 16/22* | (2019.01) | |
| *G06F 3/0482* | (2013.01) | |

(52) U.S. Cl.
CPC ........ *G16H 40/20* (2018.01); *G06F 16/2272* (2019.01); *G06N 5/04* (2013.01); *G16H 50/70* (2018.01); *G16H 70/20* (2018.01); *G06F 3/0482* (2013.01)

(58) Field of Classification Search
None
See application file for complete search history.

(56) References Cited

U.S. PATENT DOCUMENTS

| | | |
|---|---|---|
| 7,518,502 B2 | 4/2009 | Austin et al. |
| 9,710,600 B1 | 7/2017 | Dunleavy et al. |
| 10,244,377 B2 | 3/2019 | Bloechl et al. |
| 10,381,114 B2 | 8/2019 | Dunleavy |
| 10,708,970 B2 | 7/2020 | Bloechl et al. |
| 2006/0095345 A1* | 5/2006 | Ka .................... G06Q 30/0603 705/26.62 |
| 2008/0086327 A1 | 4/2008 | Cox et al. |
| 2018/0018432 A1 | 1/2018 | Dunleavy |

* cited by examiner

*Primary Examiner* — Baoquoc N To
(74) *Attorney, Agent, or Firm* — McCarter & English, LLP

(57) ABSTRACT

Systems, methods, and a non-transitory computer readable medium for a universal indexing scheme for indexing data.

14 Claims, 24 Drawing Sheets

| Procedure - Level 1 | | | 400 |
|---|---|---|---|
| | | | ⌂ Dashboard |
| | 402 | 404 | + Create Level 1 Procedure |
| ▢ Excel Export | | | |
| | System TUC L1 ↑ | TUC System TUC L1 ID | |
| 🏛ⓘ | Healthcare Facility — 406 | b738d9b2-f84b-4453-8235-c07d10515c0d — 408 | |
| 🏛ⓘ | Physician — 410 | 9520f064-d959-4d99-88dc-c084c9738690 — 412 | |
| 🏛ⓘ | Procedure — 414 | 896431f8c-301f-48b2-bbee-73902e6ae134 — 416 | |
| 🏛ⓘ | Product — 418 | c73c2908-0e56-42d4-888e-ef6dead5ad10 — 420 | |

|< < ① > >|    10 ▽    1 of 1 pages (4 items)

Items per page

FIG. 4A

| Procedure - Level 2 | | 502 | 504 | ⌂ Dashboard |
|---|---|---|---|---|
| | | | | + Create Level 2 Procedure |

| | | System TUC L2 ↑ | TUC System TUC L2 ID |
|---|---|---|---|
| 🏛 | ⓘ | Acute Care Hospital ~506 | 07b37195-ce6c-46b5-9904-8d4cddc33f02 ~508 |
| 🏛 | ⓘ | Allergist/Immunologist ~510 | 37fd1b9d-356e-4ba3-98fe-95462f95de7a ~512 |
| 🏛 | ⓘ | Ambulatory Surgical Center ~514 | 5b7e13b1-87f7-41df-a933-a2f33cbadde ~516 |
| 🏛 | ⓘ | Anesthesiologist ~518 | 9b98151f-97fb-4861-9241-0a879f15929e ~520 |
| 🏛 | ⓘ | Cardiologist ~522 | 9b0e9609-7e81-4f7a-9d1e-19e3cc542aaf ~524 |
| 🏛 | ⓘ | Dermatologist ~526 | 3b89b506-99ed-47a0-8bd8-d9bcabbc1f5a ~528 |
| 🏛 | ⓘ | Emergency Physician ~530 | b456f709-0f87-4420-8c06-f0de638e3233 ~532 |
| 🏛 | ⓘ | Endocrinologist ~534 | 6540b85e-144f-469f-a06f-c76e64e46793 ~536 |
| 🏛 | ⓘ | Family Medicine ~538 | 3ffb9cca-9df4-4a2e-8af2-4189c5d912e5 ~540 |
| 🏛 | ⓘ | Gastroenterologist ~542 | 67421b8e-600a-46f8-a6e8-bbf45db6cad0 ~544 |

|< < 1 2 3 > >|   1 of 3 pages (28 items)

10   ▽ Items per page

FIG. 5

| Procedure - Level 3 | | 600 |
|---|---|---|
| | 602 604 | ⌂ Dashboard |
| | | + Create Level 3 Procedure |

| | System TUC L3 ↑ | TUC System TUC L3 ID |
|---|---|---|
| 🏛 ⓘ | Bariatric Surgery — 606 | 79ac31d3-9f0e-48f9-a5d8-b7a13920c99d — 608 |
| 🏛 ⓘ | Cardiac Surgery — 610 | 1e07d32e-c182-4e97-8780-93b56d055b0a — 612 |
| 🏛 ⓘ | Colon and Rectal Surgery — 614 | b19d8dc4-601e-49d9-a9a7-7df11cf90de6 — 616 |
| 🏛 ⓘ | General Surgery — 618 | 8c902d80-b54e-49de-823d-9a5ddabe13f3 — 620 |
| 🏛 ⓘ | Neurological Surgery — 622 | 6db51957-d900-4f81-b4c0-3b3fc0d46454 — 624 |
| 🏛 ⓘ | Obstetrics and Gynecology Surgery — 626 | 967a5d18-c5ab-4979-aff3-29ff61f1757b — 628 |
| 🏛 ⓘ | Oncology Surgery — 630 | 27a86d6e-4e6e-45fd-90c2-cefadddc04d1 — 632 |
| 🏛 ⓘ | Ophthalmic Surgery — 634 | c32807dd-032e-466b-8d0a-b1dd20264c84 — 636 |
| 🏛 ⓘ | Oral and Maxillofacial Surgery — 638 | dd194c81-8f2e-4d3e-a0df-fcffd6ea061b — 640 |
| 🏛 ⓘ | Orthopaedic Surgery — 642 | 23022db4-12a3-4037-ad8e-be90c639352a — 644 |

|< < ① 2 > >|    10 ▽    1 of 2 pages (19 items)

Items per page

FIG. 6

| Procedure - Level 4 | 702 | 704 | | ⌂ Dashboard | + Create Level 4 Procedure |

| | System TUC L4 ↑ | TUC System TUC L4 ID |
|---|---|---|
| | Cement ~706 | 71f3d4ff-02aa-4f28-a175-004dde874de2 ~708 |
| | Fixation ~710 | b70ae01f-55a8-44a2-9e9b-20629e8a8057 ~712 |
| | Hip & Knee ~714 | 7cff08b0-39eb-4e4f-a7b6-6f41662b5320 ~716 |
| | Lower Extremity ~718 | cfb607df-a010-4e21-b963-096993f93bd9 ~720 |
| | Surgical Instrument ~722 | b3e89844-24ca-49a7-be90-cdb5dc45aea7 ~724 |
| | Suture ~726 | 198983dc-c8fb-4ec2-9462-45f6975cb568 ~728 |
| | Upper Extremity ~730 | 596a3af9-e953-4cc4-bf79-f496c567e72e ~732 |

|< < ① > >|    10 ▽    1 of 1 pages (7 items)

Items per page

FIG. 7

| Procedure - Level 5 | 802 | 804 | | 🏠 Dashboard | + Create Level 5 Procedure |

| | System TUC L5 ↑ | TUC System TUC L5 ID |
|---|---|---|
| 🗐 ⓘ | ~806 | c5f84d84-4aa7-4c3a-a025-54b330dc47cf ~808 |
| 🗐 ⓘ | Ankle ~810 | 567fdd86-c0c9-491e-b04b-10d6c61f2408 ~812 |
| 🗐 ⓘ | Arthroscope ~814 | f21eeb62-2ac6-4653-94e9-bedc628cff88 ~816 |
| 🗐 ⓘ | Upper Arm ~818 | 79ca1735-4565-46a2-9699-537159918d7 ~820 |
| 🗐 ⓘ | Foot ~822 | e7ab094b-34d0-4f4e-bc7f-9dab1a6fea17 ~824 |
| 🗐 ⓘ | General ~826 | d5a8ad8a-9d40-45d0-81db-7b91986dbf65 ~828 |
| 🗐 ⓘ | Hand & Fingers ~830 | 4f6dc971-f48c-420b-b4e3-c8da62ce6a07 ~832 |
| 🗐 ⓘ | Hip & Pelvis ~834 | 1468599b-eedd-4710-ad5e-b552d0648045 ~836 |
| 🗐 ⓘ | Knee & Thigh ~838 | 0293573a-da77-453b-a705-1399d4a57e74 ~840 |
| 🗐 ⓘ | Lower Arm & Wrist ~842 | 137f596e-9c83-4a86-8d77-043b12eb493c ~844 |

|< < ① 2 > >| 10 ▽ Items per page 1 of 2 pages (13 items)

Items per page

Physician: SMITH, JOHN

| TUC Codes | NPI Details | Top CMS CPT Code | Medicare Reimbursements | Open Payments | Taxonomy Codes | State Licence # |
|---|---|---|---|---|---|---|

☐ Excel Export

| NPI | Position | Taxonomy Code | Taxonomy Switch | Grouping | Classification | Specialization |
|---|---|---|---|---|---|---|
| 1002 | 1004 | 1004 | 1006 | 1008 | 1010 | 1012 |
| 1003000522 | 1 | 207QA0505X | Y | Allopathic & Osteopathic Physicians | Family Medicine | Adult Medicine |

< < < > > >   ① 10 ▽ Items per page

FIG. 10A

| Preference Card Library | Asset Library Lookup | Library Card Systems | | | |
|---|---|---|---|---|---|
| System TUC L1 | System TUC L2 | System TUC L3 | System TUC L4 | System TUC L5 | TUC Master Serial Number - NPI Physician ID |
| 1014 | 1016 | 1018 | 1020 | 1022 | 1024 |
| Physician | Family Medicine | Bariatric Surgery | Cement | Upper Arm | 8b17074e8-a28f-44b9-adc5-228ee7a27ed6 |

Physician

🏠 Dashboard

Data Fields Layout Diagram

⊞ Excel Export

| Npi ⋮ 1102 | Last Name ⋮ 1104 | First Name ⋮ 1106 | Credentials ⋮ 1108 | Taxonomy Primary ⋮ 1110 | Tax System TUC L1 ⋮ 1112 | Tax System TUC L2 ⋮ 1114 |
|---|---|---|---|---|---|---|
| 100300126 | SMITH | JOHN | M.D. | 207R00000X | Physician | Internal Medicine |
| 100300126 | DOE | JAMES | M.D. | 207R00000X | Physician | Internal Medicine |
| 100300126 | JOHNSON | WILLIAM | M.D. | 207R00000X | Physician | Internal Medicine |
| 100300134 | BROWN | DANIEL | M.D. | 2072P0102X | Physician | Pathology |
| 100300142 | WILLIAMS | ALEXANDER | M.D. | 207L00000X | Physician | Anesthesiologist |
| 100300407 | JONES | DAVID | D.O. | 207Q00000X | Physician | Family Medicine |
| 100300431 | MILLER | JILL | D.O. | 2084P0800X | | |
| 100300480 | WILSON | KEVIN | MD | 208600000X | | |
| 100300522 | ANDERSON | MATTEW | MD | 207QA0505X | Physician | Family Medicine |
| 100300530 | JACKSON | JANE | DO | 207R00000X | Physician | Internal Medicine |

Facility - Parents

| | CCN ID | Grandparent Facility Name | Parent Facility Name | Child Count | System TUCL1 |
|---|---|---|---|---|---|
| | 1202 | 1204 | 1206 | 1208 | 1210 |
| | 070024 | Hartford Healthcare | Backus Hospital | 7 | Healthcare Facility |
| | 070024 | Hartford Healthcare | Backus Hospital | 7 | Healthcare Facility |
| | 450853 | Baylor Scott & White Health | Baylor Scott & White Medical Center - Frisco | 2 | Healthcare Facility |
| | 670067 | Baylor Scott & White Health | Baylor Scott & White Orthopedic and Spine Hospital - Arlington | 4 | Healthcare Facility |
| | 450021 | Baylor Scott & White Health | Baylor University Medical Center | 26 | Healthcare Facility |
| | X | Baystate Health | Baystate Franklin Medical Center | 0 | Healthcare Facility |
| | 220077 | Baystate Health | Baystate Medical Center | 0 | Healthcare Facility |
| | | Baystate Health | Baystate Noble Hospital | 0 | Healthcare Facility |
| | | Baystate Health | Baystate Wing Hospital | 0 | Healthcare Facility |
| | 070009 | Hartford Healthcare | Bradley Memorial | 2 | Healthcare Facility |

＋ Create

Excel Export

|< < 1 2 3 4 5 > >| 10 Items per page

FIG. 12A

| Dashboard | | | | | |
|---|---|---|---|---|---|
| New Parent Facility 1222 | | | | | |
| System TUC L2 1212 ▼ | System TUC L3 1214 ▼ | System TUC L4 1216 ▼ | System TUC L5 1218 ▼ | TUC Master Serial Number - Parent ID 1220 | |
| Acute Care Hospital | Bariatric Surgery | Cement | Upper Armor | a8ecc1a5-71e8-4504-9e1o-79efef20c239 | |
| Acute Care Hospital | Bariatric Surgery | Cement | Upper Armor | a8ecc1a5-71e8-4504-9e1o-79efef20c239 | |
| Acute Care Hospital | Bariatric Surgery | Cement | Upper Armor | 8c55bdd2-7e34-40b1-966e-ab56eab0ab5 | |
| Acute Care Hospital | Bariatric Surgery | Cement | Upper Armor | 9056f8e-bdfe-47d6-9831-97c522118c0f | |
| Acute Care Hospital | Bariatric Surgery | Cement | Upper Armor | aeaf80cb-140a-4bed-909b-4caeb152a2c1 | |
| Acute Care Hospital | Bariatric Surgery | Cement | Upper Armor | 7efcd2fd-1985-4cb6-a11d-5f101e290738 | |
| Acute Care Hospital | Bariatric Surgery | Cement | Upper Armor | 5a464b99-baa3-4be0-bd57-531a1e6db197 | |
| Acute Care Hospital | Bariatric Surgery | Cement | Upper Armor | 6b172a65-5cb2-4bdd-b0ae-2fcaac8964a0 | |
| Acute Care Hospital | Bariatric Surgery | Cement | Upper Armor | 30de6fc9-2714-4ce1-8af3-a869dbc93e75 | |
| Acute Care Hospital | Bariatric Surgery | Cement | Upper Armor | 40d3639a-0bdc-4e1c-a524-708f6060c2a6 | |
| | | | | 1 of 5 pages (45 items) | |

PHYSICIAN: JOHN, SMITH

| TUC CODES | NPI DETAILS | TOP CMS CPT CODE | MEDICARE REIMBURSEMENTS | OPEN PAYMENTS | TAXONOMY CODES | STATE LICENCE # |
|---|---|---|---|---|---|---|
| TUC MASTER SERIAL NUMBER - PHYSICIAN ID | | | | 8B17074E8-A28F-44B9-ADC5-228EE7A27ED6 | | |
| NPI | | | | 1003000522 | | |
| REPLACEMENT NPI | | | | N/A | | |
| EIN | | | | N/A | | |
| PROVIDER ORGANIZATION NAME | | | | N/A | | |
| LAST NAME | | | | SMITH | | |
| FIRST NAME | | | | JONH | | |
| PROVIDER MIDDLE NAME | | | | J | | |
| PROVIDER NAME PREFIX TEXT | | | | DR. | | |
| PROVIDER NAME SUFFIX TEXT | | | | N/A | | |

| | |
|---|---|
| GEOG | |
| TAXONOMY PRIMARY | OBJECT OBJECT1 |
| TAXONOMY DESCRIPTION | 207Q0505X |
| HCPCS CODE | ALLOPATHIC & OSTEOPATHIC PHYSICIANS, FAMILY MEDICINE, ADULT MEDICINE |
| TOP AMOUNT | NA |
| AMOUNT | NA |
| L1 CODE | NA |
| L1 DESCRIPTION | NA |
| NPI SYSTEM TUC L1 | PHYSICIAN |
| NPI SYSTEM TUC L2 | CARDIOLOGIST |
| NPI SYSTEM TUC L3 | BARIATRIC SURGERY |
| NPI SYSTEM TUC L4 | SUTURE |
| NPI SYSTEM TUC L5 | GENERAL |
| TAX SYSTEM TUC L1 | PHYSICIAN |
| TAX SYSTEM TUC L2 | CARDIOLOGIST |
| TAX SYSTEM TUC L3 | CARDIAC SURGERY |
| TAX SYSTEM TUC L4 | SUTURE |
| TAX SYSTEM TUC L5 | GENERAL |
| CPT SYSTEM TUC L1 | PRODUCT |
| CPT SYSTEM TUC L2 | CARDIOLOGIST |
| CPT SYSTEM TUC L3 | CARDIAC SURGERY |
| CPT SYSTEM TUC L4 | SUTURE |
| CPT SYSTEM TUC L5 | ARTHROSCOPE |

FIG. 14B

SYSTEMS AND METHODS FOR AN UNIVERSAL INDEXING SCHEME FOR INDEXING DATA

BACKGROUND

Providing high quality and patient-centered health care is becoming increasingly dependent on effective and timely management of medical information. However, limited abilities to capture and/or access comprehensive medical information across organizations have been a barrier to providing high quality and patient-centered health care.

SUMMARY

In one embodiment, a method for a universal indexing scheme for indexing data is provided. The method includes generating, via an indexing engine executing on a computing device, a plurality of universally unique identifiers for a plurality of descriptive identifiers. The method also includes querying, via a data-retrieving engine executing on the computing device, at least two data sources, the at least two data sources including at least a first data source and a second data source, the first data source having a different coding scheme than the second data source. The method further includes harvesting, via the data-retrieving engine, data from the at least two data sources into a database communicatively coupled to the computing device, the data including a plurality of data items. The method also includes assigning, via the indexing engine, a descriptive identifier of the plurality of the descriptive identifiers to at least one data item of the plurality of data items, the descriptive identifier associated with a universally unique identifier of the plurality of universally unique identifiers. The method further includes associating, via the indexing engine, in the database, the universally unique identifier with the at least one data item.

In another embodiment, a system for a universal indexing scheme for indexing data is provided. The system includes at least one computing device executing an data-retrieving engine and an indexing engine. The at least one computing device is communicatively coupled to a database. The data-retrieving engine is configured to query at least two data sources, the at least two data sources including at least a first data source and a second data source, the first data source having a different coding scheme than the second data source, and harvest data from the at least two data sources into the database communicatively coupled to the computing device, the data including a plurality of data items. The indexing engine is configured to generate a plurality of universally unique identifiers for a plurality of descriptive identifiers, assign a descriptive identifier of the plurality of the descriptive identifiers to at least one data item of the plurality of data items, the descriptive identifier associated with a universally unique identifier of the plurality of universally unique identifiers, and associate in the database, the universally unique identifier with the at least one data item.

In still another embodiment, a non-transitory computer readable medium is provided. The non-transitory computer readable medium includes instructions that when executed cause a computing device to generate, via an indexing engine executing on the computing device, a plurality of universally unique identifiers for a plurality of descriptive identifiers. Execution of the instructions further causes the computing device to query, via a data-retrieving engine executing on the computing device, at least two data sources, the at least two data sources including at least a first data source and a second data source, the first data source having a different coding scheme than the second data source. Execution of the instructions also causes the computing device to harvest, via the data-retrieving engine, data from the at least two data sources into a database communicatively coupled to the computing device, the data including a plurality of data items. Execution of the instructions further causes the computing device to assign, via the indexing engine, a descriptive identifier of the plurality of the descriptive identifiers to at least one data item of the plurality of data items, the descriptive identifier associated with a universally unique identifier of the plurality of universally unique identifiers. Execution of the instructions also causes the computing device to associate, via the indexing engine, in the database, the universally unique identifier with the at least one data item.

There has thus been outlined, rather broadly, certain embodiments in order that the detailed description thereof herein may be better understood, and in order that the present contribution to the art may be better appreciated. There are, of course, additional embodiments that will be described below and which will form the subject matter of the claims appended hereto.

In this respect, before explaining the embodiments in detail, it is to be understood that the embodiments are not limited in its application to the details of construction and to the arrangements of the components set forth in the following description or illustrated in the drawings. The embodiments are capable of being practiced and carried out in various ways in addition to those described. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present embodiments. It is important, therefore, that the claims be regarded as including such equivalent constructions insofar as they do not depart from the spirit and scope of the present disclosures.

BRIEF DESCRIPTION OF THE DRAWINGS

The accompanying drawings, which are incorporated in and constitute a part of this specification, illustrate one or more embodiments taught herein and, together with the description, help to explain the embodiments. The embodiments are illustrated by way of example and should not be construed to limit the present disclosure. In the drawings:

FIG. 4A is a first sample user interface displaying sample universally unique identifiers, in accordance with an exemplary embodiment.

FIG. 5 is a second sample user interface displaying sample universally unique identifiers, in accordance with an exemplary embodiment.

FIG. 6 is a third sample user interface displaying sample universally unique identifiers, in accordance with an exemplary embodiment.

FIG. 7 is a fourth sample user interface displaying sample universally unique identifiers, in accordance with an exemplary embodiment.

FIG. 8 is a fifth sample user interface displaying sample universally unique identifiers, in accordance with an exemplary embodiment.

FIG. 9 is a sample user interface for manually assigning universally unique identifiers, in accordance with an exemplary embodiment.

FIGS. 10A-10B is a user interface displaying universally unique identifiers associated with a sample physician, in accordance with an exemplary embodiment.

FIG. 11 is a user interface displaying sample physicians, in accordance with an exemplary embodiment.

FIGS. 12A-12B is a user interface displaying sample facilities, in accordance with an exemplary embodiment.

FIGS. 14A-14B displays a data flow diagram of the data obtained from received and/or obtained from different coding schemes, in accordance with an exemplary embodiment.

Figure 1:
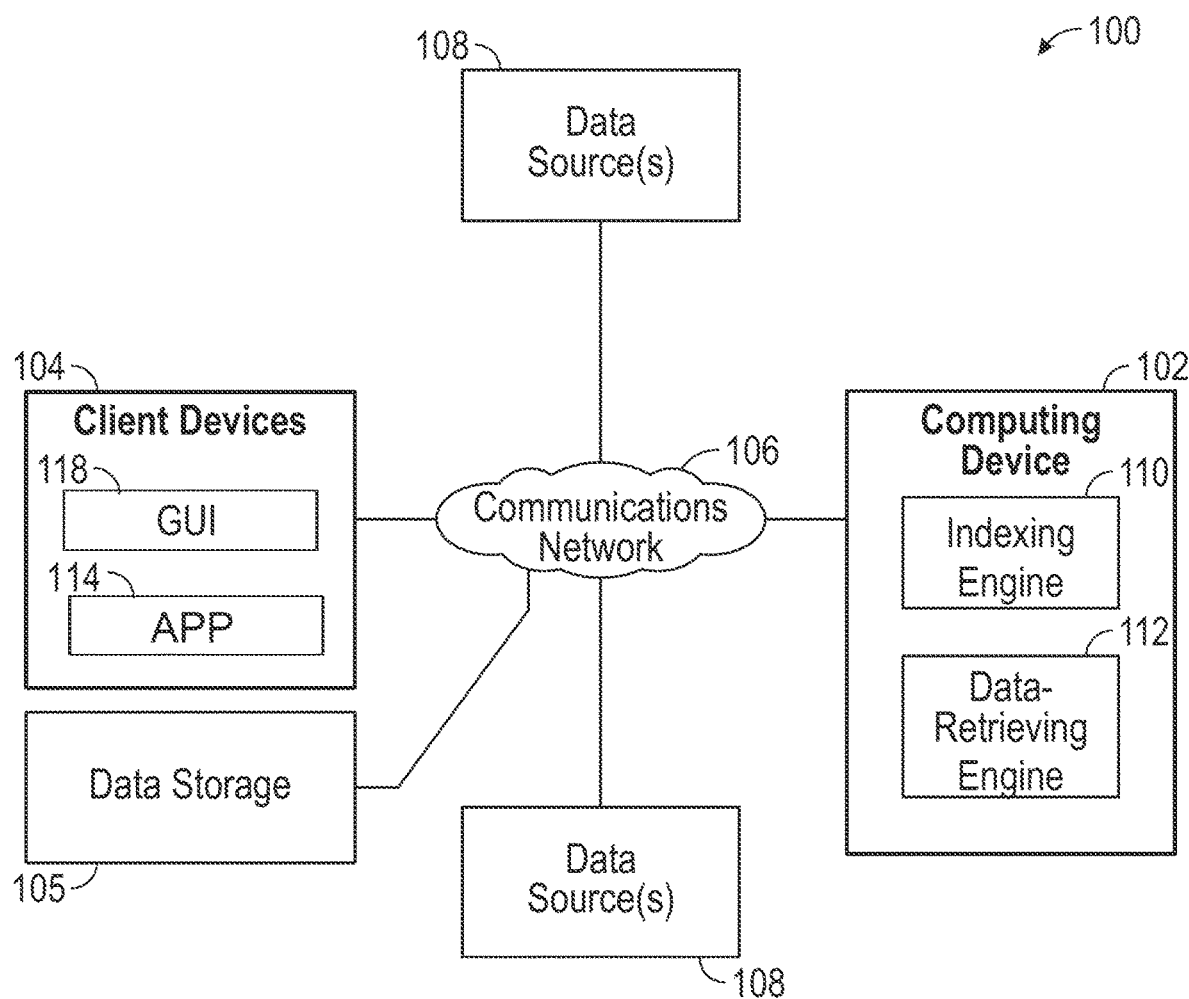
FIG. 1 is a block diagram illustrating a system for a universal indexing scheme for indexing data, in accordance with an exemplary embodiment.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION OF THE DISCLOSURE

The present disclosure provides advantageous systems and methods that provide an universal indexing scheme for indexing data received and/or obtained from at least two different coding schemes. In exemplary implementations of the present disclosure, systems, methods, and non-transitory computer readable medium are described for generating universally unique identifiers for information obtained from different coding schemes. The system includes at least one computing system executing at least an Indexing Engine and a Data-Retrieving Engine and coupled to at least one database.

The Indexing Engine generates universally unique identifiers (UUIDs) for descriptive identifiers. In an exemplary embodiment, a descriptive identifier may be, but is not limited to, a descriptive word or words chosen by a user. For example, a descriptive identifier may be "physician," "family medicine," "hospital," "knee replacement," and so forth. The user enters one or more descriptive identifiers into a user interface associated with the system. The Indexing Engine then generates a universally unique identifier for each of the entered descriptive identifiers. For example, the user enters (e.g., types via a keyboard) a descriptive identifier of "physician" into the user interface. The Indexing Engine then generates a universally unique identifier for "physician." The Indexing Engine stores the descriptive identifiers and the universally unique identifiers in the database.

The Data-Retrieving Engine is configured to obtain and/or receive data from at least two data sources or data repositories, including at least a first data source and a second data source. For example, the Data-Retrieving Engine queries the at least two data source. The first data source includes a different coding scheme than the second data source. In one embodiment, a coding scheme is a set of codes, typically defined by the numbers, words, and/or phrases, assigned to data to, for example, categorize and/or identify the data. For example, the NPI registry includes NPI numbers associated with physicians and healthcare providers, the NPI numbers used in administrative and financial transactions adopted under HIPAA. The Data-Retrieving Engine harvests data from the at least two data sources into the database communicatively coupled to Data-Retrieving Engine. The harvested data includes, but is not limited to, descriptive textual or numerical data items, such as, but not limited to, names, addresses, classifications, and specialization.

In an exemplary embodiment, the data items are parsed from the harvested data. In one embodiment, a user parses out the data items from the harvested data and adds the data items to the database. In another embodiment, the Data-Retrieving Engine parses out the data items (for example, using data recognition and/or search for data in certain formats or structures, and parses that structure) and adds the data items to the database.

The Indexing Engine assigns or maps descriptive identifiers to one or more data items of the harvested data, where each descriptive identifier is associated with a universally unique identifier. In one embodiment, the user determines which descriptive identifier (e.g., "physician") to assign to a data item (e.g., a name of a physician). This determination may be based on, for example, the descriptive identifier, information within the harvested data, and/or the data item. For example, the user assigns the descriptive identifier "physician" to the data item "John Smith, MD". In another example, the user assigns the descriptive identifier "upper arm" to the data item "John Smith, MD" because the harvested data shows that John Smith, MD, performs upper arm procedures.

In another embodiment, the Indexing Engine determines which descriptive identifier is assigned to a data item (e.g., the Indexing Engine assigns the descriptive identifier "physician" to the data item "John Smith, MD"). This determination may be based on, for example, the descriptive identifier, information within the harvested data, and/or the data item. For example, the Indexing Engine may assign all physicians names within the NPI registry the descriptive identifier "physician."

In one embodiment, once the descriptive identifiers and universally unique identifiers are generated, each descriptive identifier and/or associated universally unique identifier is stored in a database record with its own primary key. When a descriptive identifier and associated universally unique identifier is assigned to a data item, the associated primary key is assigned to the data item. In one embodiment, a data item (typically, an entity) may be linked to multiple descriptive identifiers (for example, data item "John Smith MD" may be linked to descriptive identifiers "physician" and "knee surgery"). In this embodiment, a link table in used within the database. In another embodiment, a data item may be linked to one universally unique identifier. In such an embodiment, the primary key is used directly without the use of a link table.

In some embodiments, one or more data items identified in the harvested data may already be known to the system and stored in the database. For example, "John Smith, MD" may be identified as a data item in the harvested data but already saved in the system. In such a scenario, a user and/or the Indexing Engine may assign descriptive identifiers (e.g., "upper arm") to "John Smith, MD" based on the descriptive identifiers and the data obtained from the harvested data (e.g., data shows John Smith performs upper arm surgeries). For example, the user assigns the descriptive identifier "upper arm" to the known data item "John Smith, MD" because the harvested data shows that John Smith, MD, performs upper arm procedures. In such an embodiment, the system (e.g., the Indexing Engine) or a user assigns descriptive identifiers to the known data item (e.g., a physician) based on the retrieved data.

The Indexing Engine assigns or maps the universally unique identifiers to the data items to uniquely identifies the data items in accordance with the one or more assigned universally unique identifiers. This assignment occurs regardless of the coding scheme used by a particular data source. The Indexing Engine associates, in the database, each data item with that data item's assigned descriptive identifier(s) and associated universally unique identifier(s). Thus, the disclosed systems and methods enables cross referencing the at least two or more different coding schemes. Similarly, the disclosed systems and methods provide functionalities that support capture of and/or access to comprehensive information across organizations and/or databases, thereby improving important information-based operations that may involve third party operations (e.g., the FDA, insurance providers and medical equipment/pharmaceutical suppliers).

As a non-limiting real world example, a first coding scheme in a first data repository may identify "John Smith MD" as a physician using the term "doctor" and a second coding scheme in a second data repository different from the first coding scheme may identify "John Smith MD" as a physician by using the code "00001"; however, in both scenarios, the Indexing Engine assigns the descriptive identifier "physician" and associated universally unique identifier to "John Smith MD." Conversely, if a first coding scheme identifies "John Smith MD" as a physician using the term "doctor" and a second different coding scheme identifies "John Smith MD" as a hospital by using the code "00002," the Indexing Engine assigns the descriptive identifier for "physician" and the descriptive identifier for "hospital" to "John Smith MD." The latter assignment indicates that there is an data issue with one of the repositories.

In some embodiments, the system may be fully automated, such that it will receive the data from one or more data sources, parse out particular data items (for example, physician names using data recognition, search for data in certain format or structure, etc.) and automatically assigns a descriptive identifier associated with a universally unique identifier to each data item. In other embodiments, a user reviews the data from one or more data sources, identifies particular data items, and assigns a universally unique identifier to each data item.

The universally unique identifiers generated according to the present disclosure will generally integrate two or more data sources with different coding schemes. The two or more data sources may include, but are not limited to, the following data sources:

Global Unique Device Identification Database (GUDID), which may include data/data fields related to individual devices, device manufacturers/distributors, device identifiers, device product codes, contact information for manufacturers/distributors, and premarket submissions related to the devices. The GUDID database includes GUDID device information (e.g., DUNS number, company name, etc.), GUDID identifiers (e.g., device ID, GTIN, etc.), GUDID product codes, GUDID contacts (e.g., phone, email, etc.), and GUDID premarket submissions (e.g., submission number, 510k, etc.).

U.S. Food and Drug Administration (FDA) Database, which includes FDA registration information for a device, owner/operator data relative to the device, official correspondent for FDA purposes relative to a device, and FDA clearance information (e.g., 510(k) information, PMA information, etc.). The FDA database include FDA registration information (e.g., registration number, name addresses, city, state, country, zip, postal code), owner operator information (e.g., contact ID, firm name, owners operator number), official correspondent information (e.g., contact ID, first names, middle name, last name, sub account company name, phone number), and FDA 510(k) information (e.g., id number, applicant, address, product code, device name, 510k).

GS1 Database, which may include GS1's interlocking numbering systems, i.e., GTIN for product identification, GLN for physical locations, and the EPCIS system for transaction information. The GS1 Company Database provides basic company information for GS1 member. The GS1 Database includes information on device manufacturers and UPC (e.g., GTIN, company name, DUNS number, device identifier, GLN, GS1 company prefix, GS1 UPC prefix, GS1 company name, GS1 company address, GS1 company city, GS1 company country, parent GGLN, location name, etc.).

Global Medical Device Nomenclature (GMDN) Database, which is a system of internationally agreed descriptors used to identify medical device products. The GMDN Database lists terms, which are currently available to name and describe medical devices, The GMDN Term is made up of several data elements, including the Term Name, GMDN Code and a Definition.

CPT® Codes Database, which is a medical code set published by the American Medical Association (AMA) and used to report medical services and procedures (surgical and diagnostic) for reimbursement.

National Provider Identifier (NPI) Registry database, which is a directory of active NPI records. Healthcare providers acquire unique 10-digit NPIs to identify themselves in a standard way throughout their industry. Individuals or organizations apply for NPIs through the CMS National Plan and Provider Enumeration System. After obtaining an NPI, parts of the NPI record that have public relevance are published, including the provider's name, specialty (taxonomy) and practice address. A taxonomy code is a unique 10-character code that designates a provider's classification and specialization.

DUNS® Database and/or equivalent or complementary corporate/financial information database, which may include company name, identification number, address information, business activity codes, and the like as it relates to a device manufacturer and/or distributor. DUNS® is a business identification system operated by the private company Dun & Bradstreet®. DUNS® numbers are required for medical device establishments to comply with FDA Unique Device Identifier (UDI) regulations. The DUNS database includes DUNS numbers and information associated with medical device (e.g., company name, address, zip, city, country, country code, postal identifier, PO box, town, phone, fax, executive name, business activity code, etc.).

These databases may be periodically updated to reflect the most up-to-date information available in the associated database.

In an exemplary embodiment, the universally unique identifiers are based on the UUID datatype (see, for example, https://en.wikipedia.org/wiki/universally_unique__identifier, which is incorporated herein in its entirety). In such an embodiment, the Indexing Engine generate the universally unique identifiers using the PostgreSQL function call: uuid_generate_v4( ). Each universally unique identifiers is guaranteed to be unique across space and time, regardless where they were generated. In an alternative embodiment, the universally unique identifiers may be defined as a multi-unit string of characters of fixed or variable length. In such example, "physician" may be mapped to unique identifier "0001xby786", "hospital" may be mapped to unique identifier "0002vyu926", and so forth. The mapping may entail numbers, letters and other symbols. Each time a new descriptive identifier is added to the database of the present disclosure, a new unique identifier would be assigned to such descriptive identifier. Alternative methods for implementation of the universally unique identifiers may be implemented according to the present disclosure.

In one embodiment, a user interface may be used to search for and display the data items and/or the assigned universally unique identifiers. For example, a user may search via the user interface for all data items assigned a descriptive identifier associated with "physician." In such an example, the user interface displays record entries associated with the corresponding universally unique identifier for the descriptive identifier.

In some embodiments, the Indexing Engine generates a master universally unique identifier for a combination of universally unique identifiers that uniquely identifies the combination of universally unique identifiers.

In some embodiments, a first data item and a second data item may be the same or substantially similar (e.g., "doctor" and "physician") and receive the same descriptive identifier (e.g., "physician") associated with a universally unique identifier. This enables cross referencing between the two different coding schemes and facilitates searching of information.

The described systems and methods support and/or facilitate high quality and patient-centered health care. The described systems and methods improve the quality of information associated with healthcare, which assists, inter alia, in adverse event reporting, quickly identifying product problems, better targeting of recalls, billing, and improved patient safety. The universally unique identifiers serve as a foundational standard on which to compare and reference information across health care delivery systems. The universally unique identifiers of the present disclosure provides an efficient gateway to identify potentially critical information, e.g., a facility's device inventory, procedures performed by physicians, billing errors, and more. As data can originate from many sources, including physicians, device manufacturers, distributors, GPOs, billing companies, and surgical/healthcare facilities, the described system and methods allow/facilitate efficient and effective management and aggregation of healthcare related information, and seamlessly link this information by way of the universally unique identifiers, thereby ensuring data synchrony, consistency, and rapid updates.

FIG. 1 is a block diagram illustrating a system 100 for a universal indexing scheme for indexing data, in accordance with an exemplary embodiment. The system 100 includes at least one computing device 102, at least one client device 104, at least one storage device 105, at least one network 106, and at least one data source 108. The storage device 105 may be a database located on the computing device 102 or in some other storage location communicatively coupled to the computing device 102. The computing device 102 is configured to execute an Indexing Engine 110 and a Data-Retrieving Engine 112. The Data-Retrieving Engine 112 is configured to retrieve data from the data sources 108. The Indexing Engine 103 is configured to generate universally unique identifiers for the retrieved data, and store the data and/or the universally unique identifiers in the data storage devices 105.

The computing device 102 can be a physical computing device, a virtual computing device, or multiple physical and virtual computing devices functioning as one computing device. The computing device 102 can be a cloud-based system providing computational functionality remote from the facility where the system is deployed. The computing device 102 can operate on a software stack including an operating system including but not limited to Microsoft Windows-based distributions and *nix-based distributions.

Some embodiments include additionally software support for the operation of the computing device 102. The Indexing Engine 110 and a Data-Retrieving Engine 112 can be an application or a suite of applications coded to operate in the environment provided by the computing device 102. The Indexing Engine 110 and a Data-Retrieving Engine 112 can be implemented in, but not limited to, C++, JAVA, and C#. In some embodiments, the Data-Retrieving Engine 112 can be implemented in multiple languages with bindings and application programming interfaces allowing different parts of the Data-Retrieving Engine 112 to interface with the data sources 108.

A network 106 interface can be utilized in embodiments of the system. The network 106 can be a wide area network (WAN) or the Internet. In one embodiment, compatible data packets can include data packets with transmission control protocol (TCP) or user datagram protocol (UDP) routing information. The network 106 can interface with the computing device 102, the client device 104, and other networks. The network 106 can be a combination of wired and wireless connection inclusively.

The client device 104 can be attached to the network 106. The client device 104 can include a graphical user interface (GUI) 118. In some embodiments, the client device 104 can be implemented at a personal computing device, such as a smart phone, tablet, laptop, or desktop computer. The client device 104 can have network interface functionality so that it can interface with the network 106. The client device 104 can operate on a software stack including an operating system including but not limited to Microsoft Windows-based distributions, Apple iOS distributions and *nix-based distributions, including the Android operating system. The client device 104 can include support software stacks to implement graphical elements of the GUI 118. The GUI 118 can be implemented in common programming languages, including but not limited to JAVA and Objective-C, and APIs for interacting with client device 104 subsystems.

The GUI 118 can be configured to display the descriptive identifiers and universally unique identifiers described herein and data obtained from the data sources 108 and stored in data storage device 105. The GUI 118 may be associated with an application 114 installed on a number of different locations including, but not limited to, work stations, computers, general purpose computers, Internet appliances, hand-held devices, wireless devices, portable devices, wearable computers, cellular or mobile phones, portable digital assistants (PDAs), smart phones, tablets, ultrabooks, netbooks, laptops, desktops, multi-processor systems, microprocessor-based or programmable consumer electronics, network PCs, mini-computers, and the like. The application 114 may connect to network 106 via a wired or wireless connection. The application 114 may include one or more applications such as, but not limited to, a web application and/or a mobile application to enable communication with the computing device 102. Computing device 102 includes one or more computers or processors configured to communicate with the application 114 via network 106.

Data storage 105 may include one or more storage devices for storing files and/or data retrievable by computing device 102. Data storage 105 and computing device 102 may be located at one or more geographically distributed locations from each other. Alternatively, Data storage 105 may be included within computing device 102.

Below is a non-limiting real world example of the described system 100 providing an universal indexing scheme for indexing data obtained from two different coding schemes.

The Data-Retrieving Engine 110 obtains data from a NPI database (a first data source 108), which has millions of records on health care providers. The NPI database includes taxonomy codes associated with physicians. A taxonomy code is a unique 10-character code that designates a classification and a specialization of a physician. In one embodiment, the Data-Retrieving Engine 110 extracts the taxonomy codes from the obtained data using word parsing. In an alternative embodiment, a user extracts the taxonomy codes from the obtained data. The Indexing Engine 110 and/or a user creates descriptive identifiers associated with classifications (for example, "healthcare facility", "physician", "procedure", "product", etc.) and specializations (for example, "pathology", "internal medicine", "family medicine", etc.). The Indexing Engine 110 assigns a universally unique identifier to each descriptive identifier. The Indexing Engine 110 and/or the user assigns descriptive identifiers to physicians based, for example, on the taxonomy code, thereby associating the universally unique identifiers with the physician. Universally unique identifiers for the classifications may be classified under a first level (L1) and universally unique identifiers for the specializations may be classified under a second level (L2). The physicians may be data items identified in the data obtained from a NPI database.

The Data-Retrieving Engine 110 also obtains Medicare medical billing information from the CMS Medicare payment database (a second data source 108). The CMS Medicare payment database lists procedures performed by physicians. The CMS Medicare payment database uses a different coding scheme than the NPI database. In one embodiment, the Data-Retrieving Engine 110 extracts the procedure codes from the obtained data using word parsing. In an alternative embodiment, a user extracts the procedure codes from the obtained data. The Indexing Engine 110 and/or a user creates descriptive identifiers associated with procedures (for example, "cardiac surgery", "oncology", "transplant surgery", etc.). The Indexing Engine 110 assigns a universally unique identifier to each descriptive identifier. The Indexing Engine 110 and/or the user assigns descriptive identifiers to the physicians based on the procedure codes, thereby associating the universally unique identifiers with the physicians. Universally unique identifiers for the procedures may be classified under a third level (L3).

Additional data sources may be obtained and further descriptive identifiers and universally unique identifiers may be assigned to the physicians. For example, the system may obtain CPT codes (coding scheme for procedure), DRG codes (used at facility end), and ICD-9 codes. These are all independent coding schemes that can be incorporated into the described system.

Figure 2:
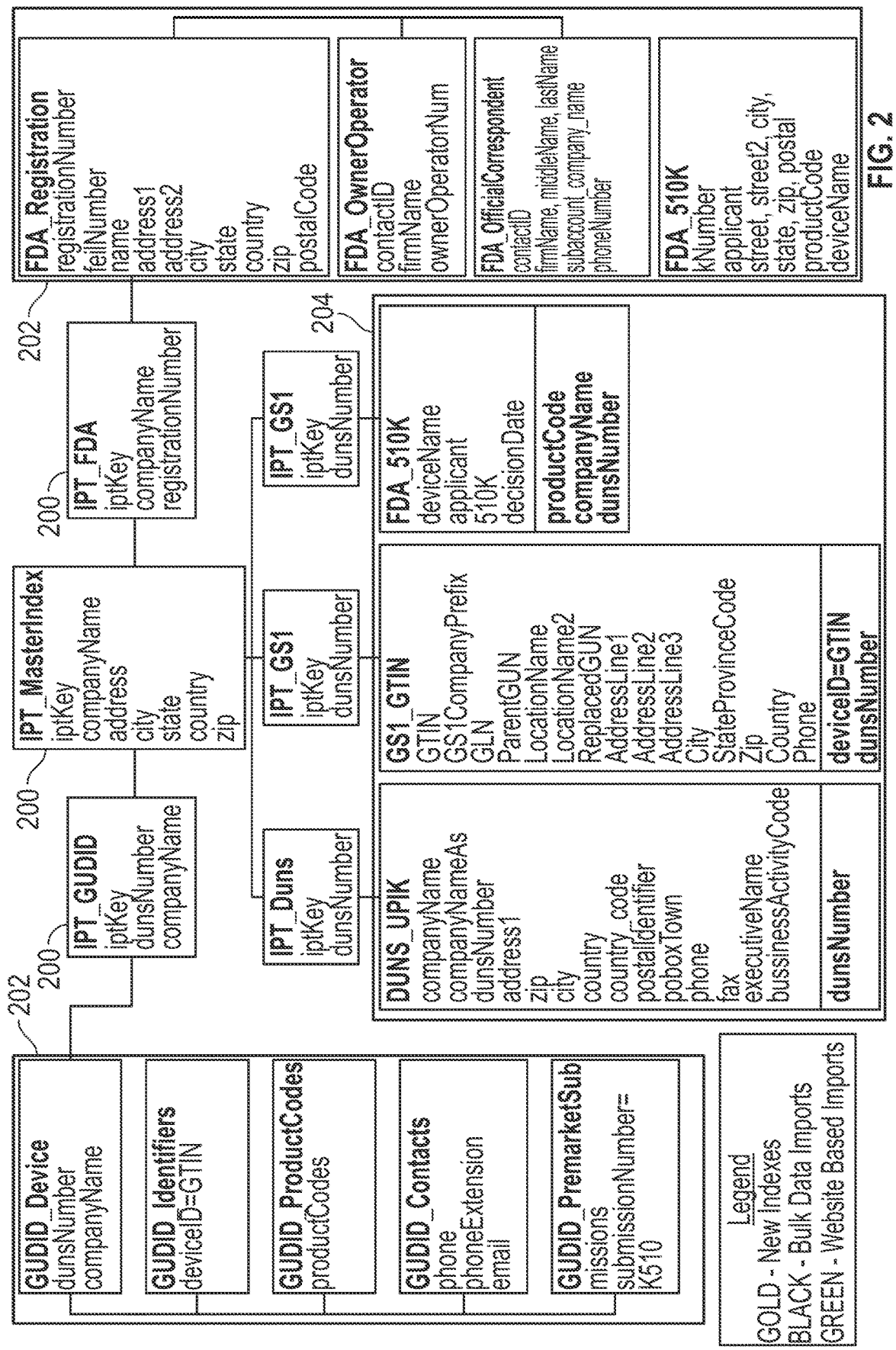
FIG. 2 is a block diagram illustrating an illustrative indexing scheme for indexing data using the system of FIG. 1, in accordance with an exemplary embodiment.

FIG. 2 is a block diagram illustrating an illustrative indexing scheme for indexing data retrieved from different coding schemes using the system 100 of FIG. 1, in accordance with an exemplary embodiment. A computing device (e.g., computing device 102) retrieves data from one or more data sources. For example, the computing device may obtain the data via a bulk data import 202 and/or a website based import 204. A bulk data import 202 may involve, for example, importing data from a third-party system using an Excel file(s) or a CVS file(s) and/or loading data from data file(s) from a third-party system into a SQL Server table. A website based import 204 may involve, for example, importing data from a website to an Excel file(s). The integration of the various data from the various data sources to generate the universally unique identifiers may be effectuated in various forms according to the present disclosure. The computing device retrieves data from the data sources and stores the data within a database communicatively coupled to the computing device.

Figure 3:
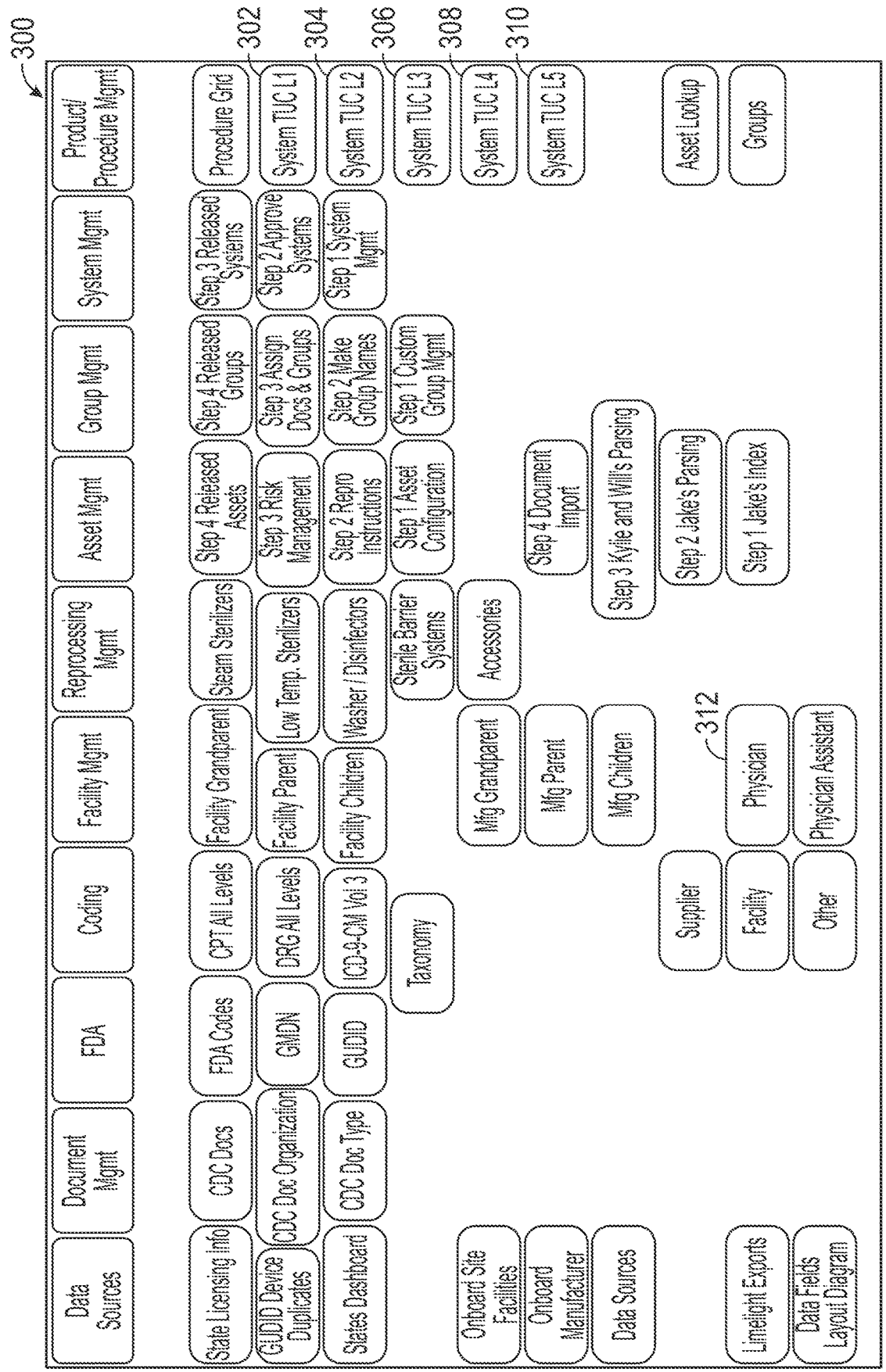
FIG. 3 is a user interface displaying a sample home page for accessing the universal indexing scheme, in accordance with an exemplary embodiment.

FIG. 3 is a graphical user interface 300 displaying a sample home page 302 for accessing the universal indexing scheme, in accordance with an exemplary embodiment. The user interface 300 includes graphical buttons used for selecting and displaying information. In an exemplary embodiment, a user can selects graphical buttons 302, 304, 306, 308, and/or 310 to view descriptive identifiers associated with universally unique identifiers. The user interface 300 may further include graphical buttons for viewing information obtained from data sources, such as, but not limited to, a graphical button 312 for viewing physicians. For example, a user can selects graphical buttons 312 to view information associated with physicians retrieved from the data sources (e.g., information retrieved from the FDA, NPI, etc.), including universally unique identifiers associated with the physicians. Each user interface associated with graphical buttons 302, 304, 306, 308, 310, and 312 are described in detail herein.

An application (for example, application 114) may implement the user interface 300 via a display including a display monitor and user input or control devices including a keyboard and a mouse. The display is used for input and output of a wide variety of information that may be associated with entering and viewing information, including the universally unique identifiers.

As shown in FIG. 3 and further illustrated in FIGS. 4-8, users have access to descriptive identifiers associated with universally unique identifiers at five (5) levels. Each graphical button 302, 304, 306, 308, and 310 displays descriptive identifiers and universally unique identifiers generated at a different level. For example, each level may be directed to descriptive identifiers within a related set. For example, the graphical button 302 may be associated with a user interface for a first level directed to descriptive identifiers associated with a medical type (e.g., healthcare facility, physician, procedure, product). The graphical button 304 may be associated with a user interface for a second level directed to descriptive identifiers associated with a specialization (e.g., acute care hospital, allergist, cardiologist, etc.), and so forth. It is appreciated that while five (5) levels are illustrated, the system can include any number of levels.

FIG. 4A is a sample graphical user interface 400 displaying descriptive identifiers associated with universally unique identifiers, in accordance with an exemplary embodiment. The user interface 400 includes descriptive identifiers within a first level. The first level includes descriptive identifiers associated with a medical type. In the exemplary embodiment, the descriptive identifiers include a healthcare facility, physician, procedure, and product. However, while these four (4) medical types are illustrated, the system can include any number of descriptive identifiers associated with a medical type. The system generates a universally unique identifier for each descriptive identifiers.

More specifically, the user interface 400 includes a first column 402 including descriptive identifiers and a second column 404 including universally unique identifiers associated with the descriptive identifiers. For example, the user interface 400 illustrates a descriptive identifier "Healthcare Facility" 406 associated with a universally unique identifier 408, a descriptive identifier "Physician" 410 associated with a universally unique identifier 412, a descriptive identifier "Procedure" 414 associated with a universally unique identifier 416, and a descriptive identifier "Product" 418 associated with a universally unique identifier 420.

In one embodiment, the system (e.g., the Indexing Engine) automatically creates the descriptive identifiers. For example, the system may automatically create a list of known surgical procedures as the descriptive identifiers and generate a universally unique identifier for each descriptive identifier. The system may create the descriptive identifiers using a predefined list of terms, data obtained from the data sources, or using deep learning/artificial intelligence.

Figure 4B:
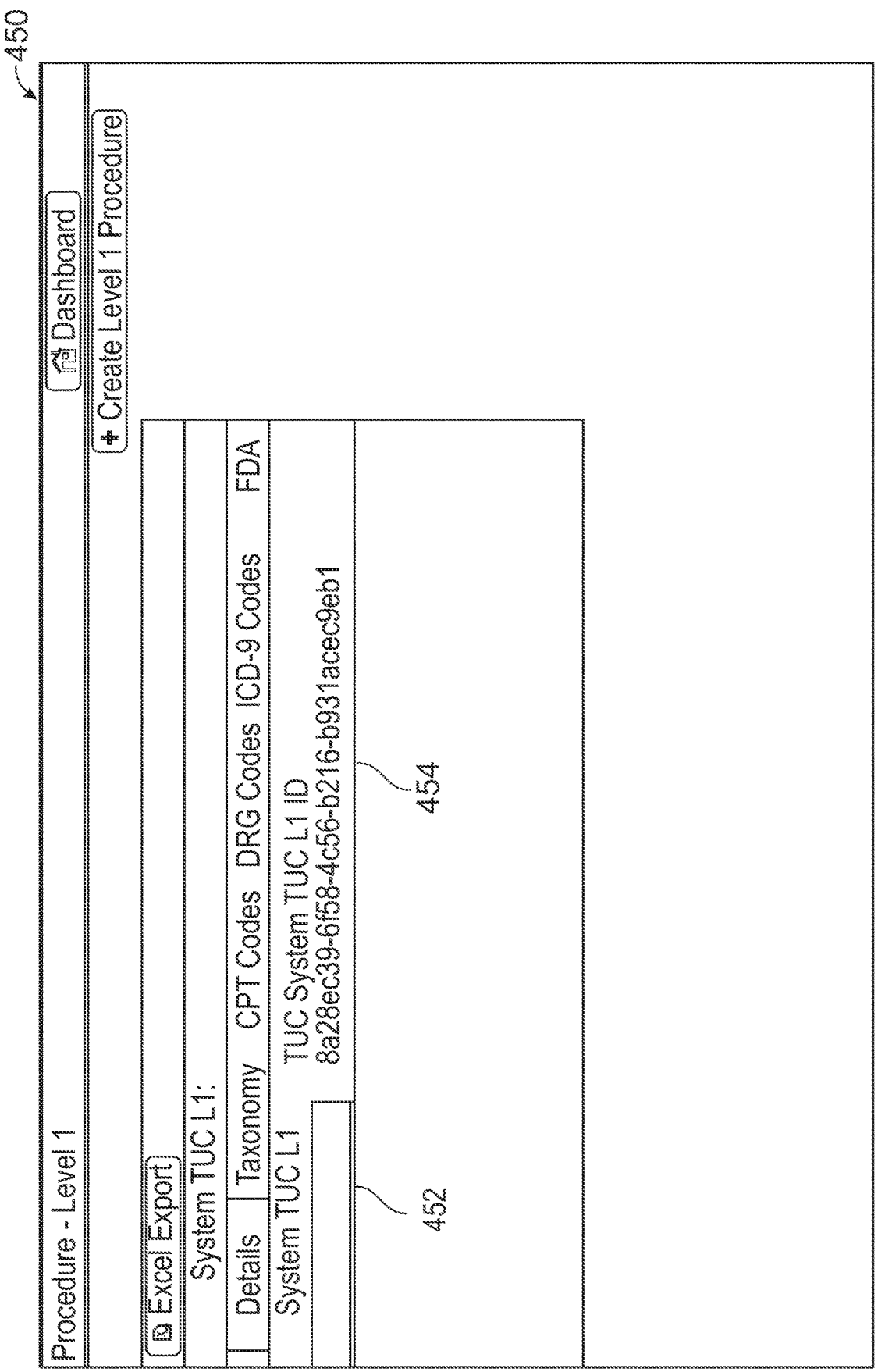
FIG. 4B is a sample user interface for creating a descriptive identifier associated with a universally unique identifier, in accordance with an exemplary embodiment.
Figure 13A:
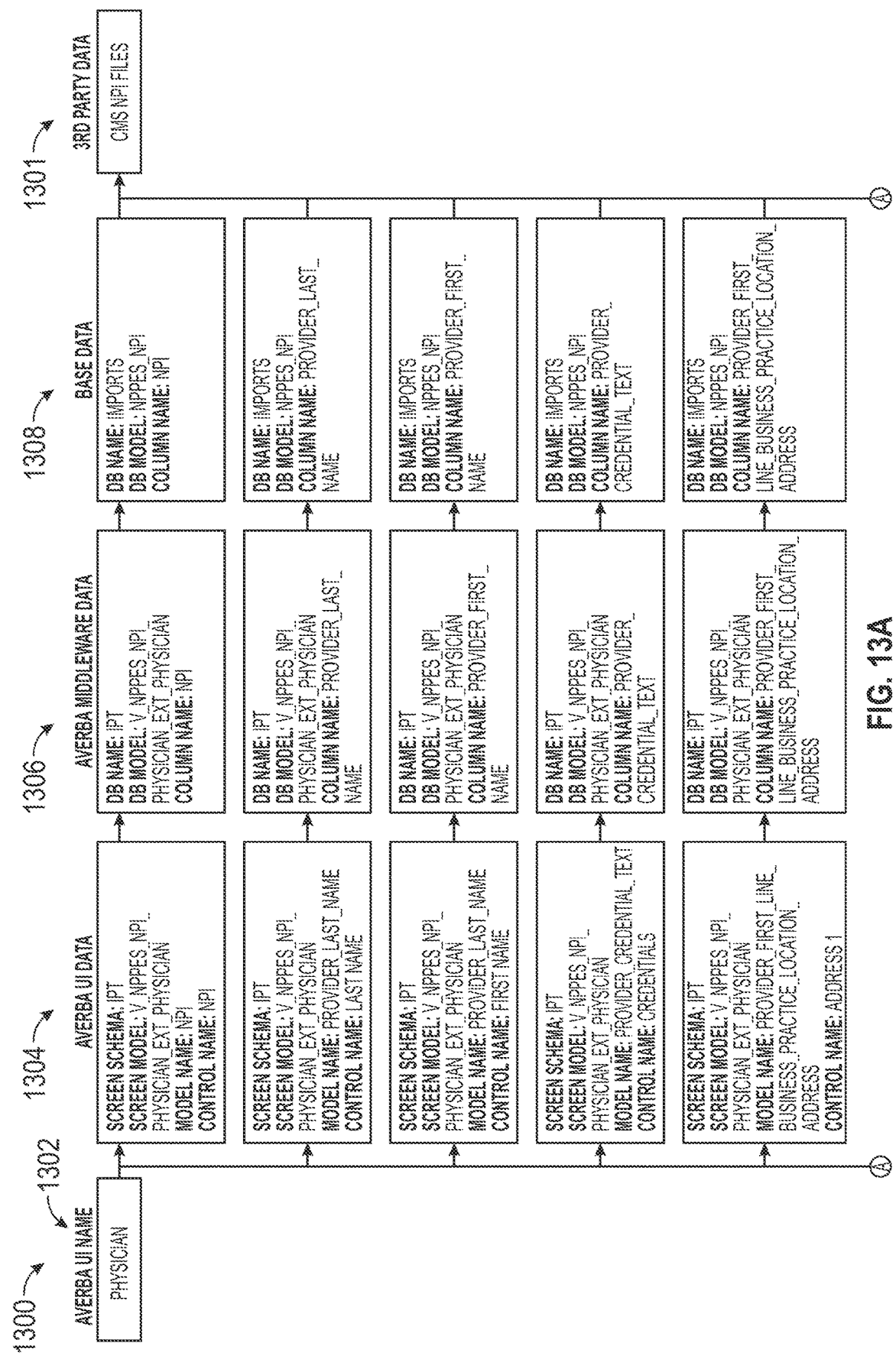
FIGS. 13A-13E displays the data linage 1300 through the implemented data layers in the technology stack of the system, in accordance with an exemplary embodiment.
Figure 13B:
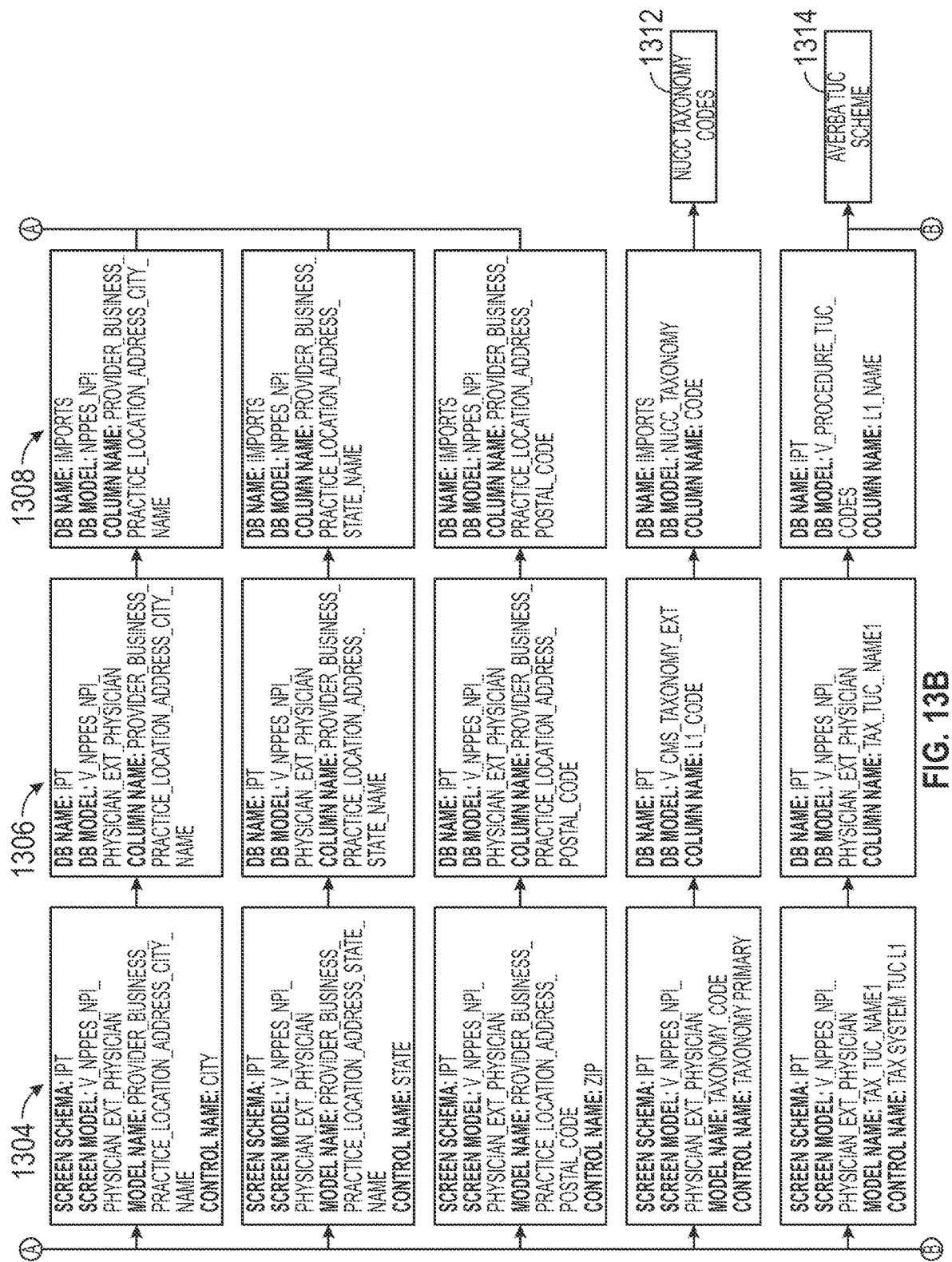
Figure 13C:
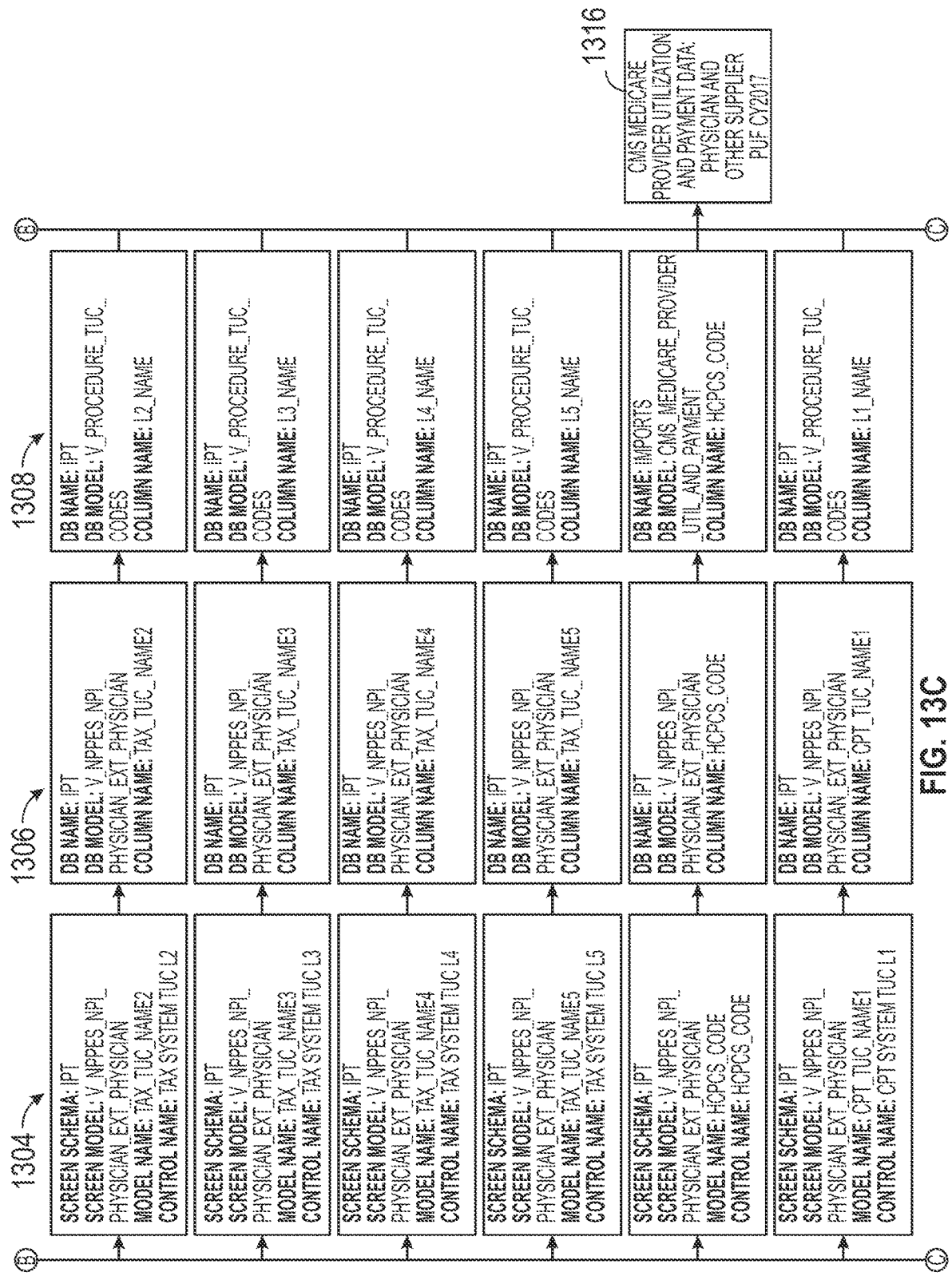
Figure 13D:
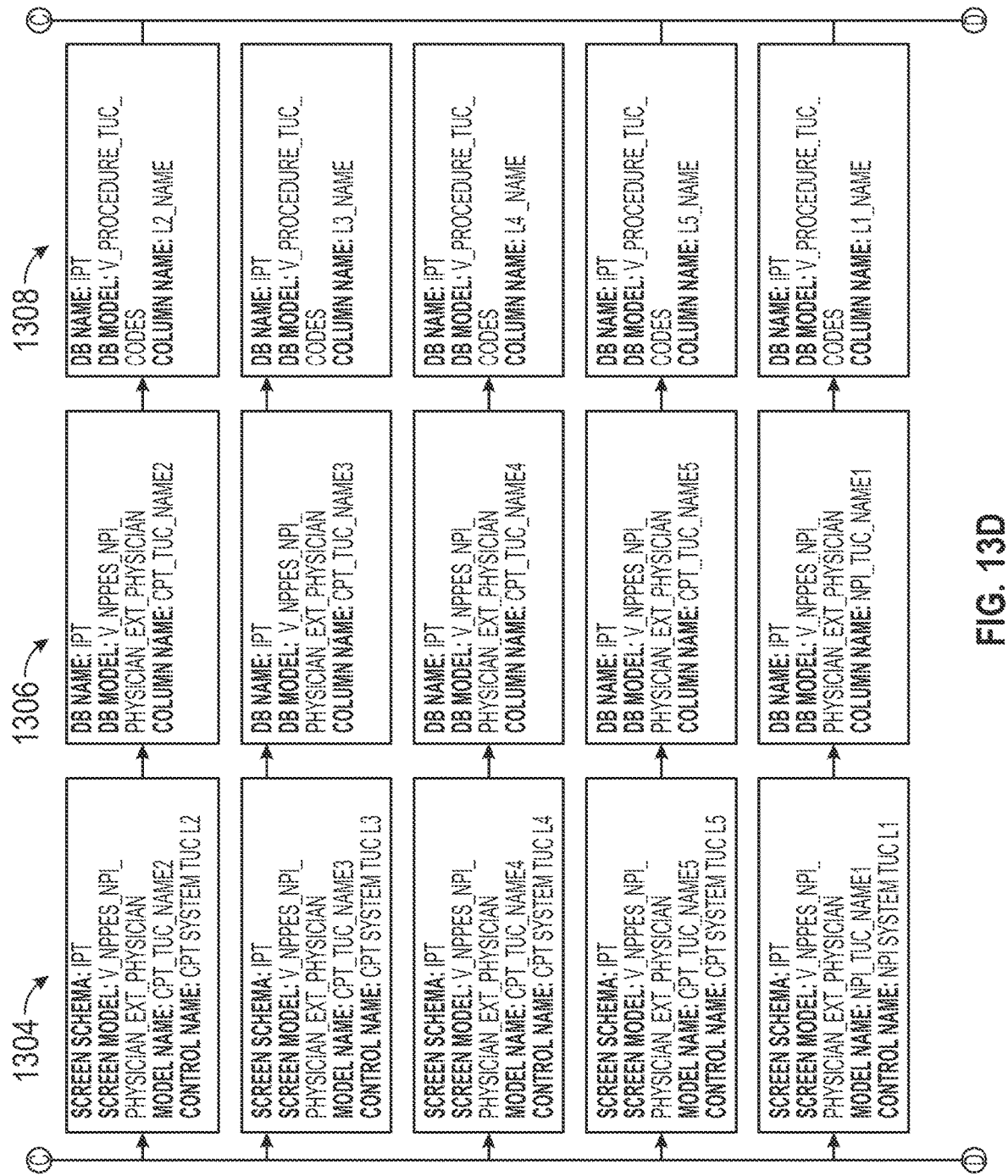
Figure 13E:
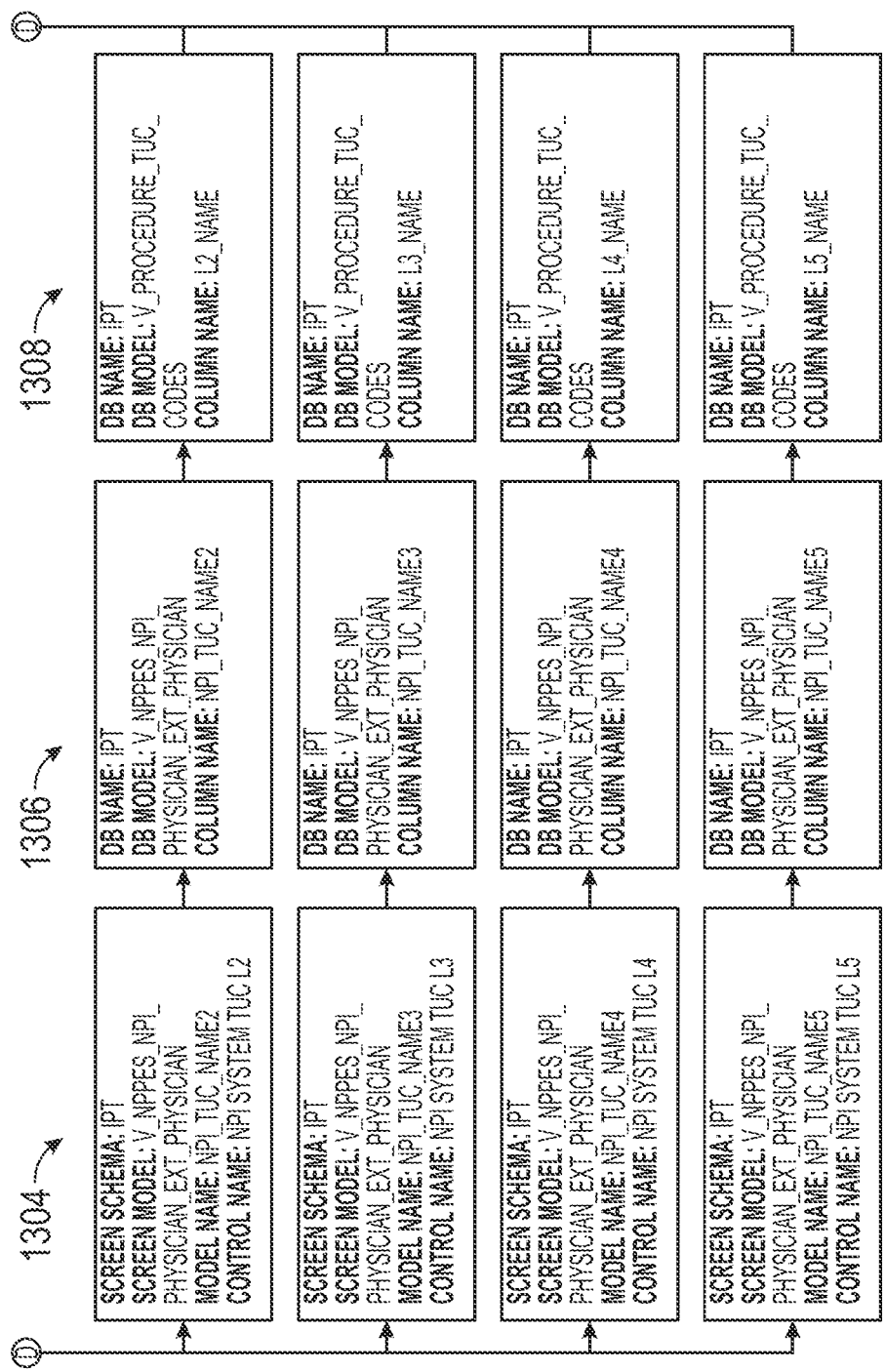

In another embodiment, a user manually creates the descriptive identifiers, as shown in FIG. 4B.

Once a descriptive identifier is created and associated with a universally unique identifier, the descriptive identifier and the universally unique identifier appear in the user interface 400, with each descriptive identifier located under the first column 402 and the associated universally unique identifiers located under the second column 404.

FIG. 4B is a sample graphical user interface 450 for creating a descriptive identifier associated with a universally unique identifier, in accordance with an exemplary embodiment. The user interface 450 includes a text field 452 in which a user can enter text identifying a name of a descriptive identifier. For example, a user can create a descriptive identifier "Physician" by entering "Physician" within the text field 452 and pressing "return" or "enter" on a keyboard communicatively coupled to user interface 450. Once the descriptive identifier is entered and transmitted to the system, the system associates the descriptive identifier with the generated universally unique identifier 454. The descriptive identifier and the associated universally unique identifier may then appear in the user interface 400.

FIG. 5 is a sample graphical user interface 500 displaying descriptive identifiers associated with universally unique identifiers, in accordance with an exemplary embodiment. The user interface 500 includes descriptive identifiers associated with universally unique identifiers within a second level. The second level includes descriptive identifiers associated with a specialty. As described herein, the system or a user creates the descriptive identifiers. In the exemplary embodiment, the descriptive identifiers include an acute care hospital, allergist/immunologist, ambulatory surgical center, anesthesiologist, cardiologist, dermatologist, emergency physician, endocrinologist, family medicine, and gastroenterologist. However, while these ten (10) medical types are illustrated, the system can include any number of descriptive identifiers associated with a specialty. The system generates a universally unique identifier for each descriptive identifiers.

More specifically, the user interface 500 includes a first column 502 including descriptive identifiers and a second column 504 including universally unique identifiers associated with the descriptive identifiers. For example, the user interface 500 illustrates a descriptive identifier "Acute Care Hospital" 506 associated with a universally unique identifier 508, a descriptive identifier "Allergist/Immunologist" 510 associated with a universally unique identifier 512, a descriptive identifier "Ambulatory Surgical Center" 514 associated with a universally unique identifier 516, a descriptive identifier "Anesthesiologist" 518 associated with a universally unique identifier 520, a descriptive identifier "Cardiologist" 522 associated with a universally unique identifier 524, a descriptive identifier "Dermatologist" 526 associated with a universally unique identifier 528, a descriptive identifier "Emergency Physician" 530 associated with a universally unique identifier 532, a descriptive identifier "Endocrinologist" 534 associated with a universally unique identifier 536, a descriptive identifier "Family Medicine" 538 associated with a universally unique identifier 540, and a descriptive identifier "Gastroenterologist" 542 associated with a universally unique identifier 544.

FIG. 6 is a sample graphical user interface 600 displaying descriptive identifiers associated with universally unique identifiers, in accordance with an exemplary embodiment. The user interface 600 includes descriptive identifiers and universally unique identifiers associated with a third level. As described herein, the system or a user creates the descriptive identifiers. The third level includes descriptive identifiers associated with a surgery type. In the exemplary embodiment, the descriptive identifiers include bariatric surgery, cardiac surgery, colon and rectal surgery, general surgery, neurological surgery, obstetrics and gynecology surgery, oncology surgery, ophthalmic surgery, oral and maxillofacial surgery, and orthopedic surgery. However, while these ten (10) surgery types are illustrated, the system can include any number of descriptive identifiers associated with a surgery type. The system generates a universally unique identifier for each descriptive identifiers.

More specifically, the user interface 600 includes a first column 602 including descriptive identifiers and a second column 604 including universally unique identifiers associated with the descriptive identifiers. For example, the user interface 600 illustrates a descriptive identifier "Bariatric Surgery" 606 associated with a universally unique identifier 608, a descriptive identifier "Cardiac Surgery" 610 associated with a universally unique identifier 612, a descriptive identifier "Colon and Rectal Surgery" 614 associated with a universally unique identifier 616, a descriptive identifier "General Surgery" 618 associated with a universally unique identifier 620, a descriptive identifier "Neurological Surgery" 622 associated with a universally unique identifier 624, a descriptive identifier "Obstetrics and Gynecology Surgery" 626 associated with a universally unique identifier 628, a descriptive identifier "Oncology Surgery" 630 associated with a universally unique identifier 632, a descriptive identifier "Ophthalmic Surgery" 634 associated with a universally unique identifier 636, a descriptive identifier "Oral and Maxillofacial Surgery" 638 associated with a universally unique identifier 640, and a descriptive identifier "Orthopedic Surgery" 642 associated with a universally unique identifier 644.

FIG. 7 is a sample graphical user interface 700 displaying descriptive identifiers associated with universally unique identifiers, in accordance with an exemplary embodiment. The user interface 700 includes descriptive identifiers and universally unique identifiers associated with a fourth level. As described herein, the system or a user creates the descriptive identifiers. The fourth level includes descriptive identifiers associated with a surgery type. In the exemplary embodiment, the descriptive identifiers include cement, fixation, hip and knee, lower extremity, surgical instrument, suture, and upper extremity. However, while these seven (7) surgery types are illustrated, the system can include any number of descriptive identifiers associated with a surgery type. The system generates a universally unique identifier for each descriptive identifiers.

More specifically, the user interface 700 includes a first column 702 including descriptive identifiers and a second column 704 including universally unique identifiers associated with the descriptive identifiers. For example, the user interface 700 illustrates a descriptive identifier "Cement" 706 associated with a universally unique identifier 708, a descriptive identifier "Fixation" 710 associated with a universally unique identifier 712, a descriptive identifier "Hip and Knee" 714 associated with a universally unique identifier 716, a descriptive identifier "Lower Extremity" 718 associated with a universally unique identifier 720, a descriptive identifier "Surgical Instrument" 722 associated with a universally unique identifier 724, a descriptive identifier "Suture" 726 associated with a universally unique identifier 728, and a descriptive identifier "Upper Extremity" 730 associated with a universally unique identifier 732.

FIG. 8 is a sample graphical user interface 800 displaying descriptive identifiers associated with universally unique identifiers in accordance with an exemplary embodiment. The user interface 800 includes descriptive identifiers and universally unique identifiers associated with a fifth level. As described herein, the system or a user creates the descriptive identifiers. The fifth level includes descriptive identifiers associated with a surgery type. In the exemplary embodiment, the descriptive identifiers include ankle, arthroscope, upper arm, foot, general, hand and fingers, hip and pelvis, knee and thigh, and lower arm and wrist. However, while these nine (9) surgery types are illustrated, the system can include any number of descriptive identifiers associated with a surgery type. The system generates a universally unique identifier for each descriptive identifiers.

More specifically, the user interface 800 includes a first column 802 including descriptive identifiers and a second column 804 including universally unique identifiers associated with the descriptive identifiers. For example, the user interface 800 illustrates a descriptive identifier "ankle" 810 associated with a universally unique identifier 812, a descriptive identifier "arthroscope" 814 associated with a universally unique identifier 816, a descriptive identifier "upper arm" 818 associated with a universally unique identifier 820, a descriptive identifier "foot" 822 associated with a universally unique identifier 824, a descriptive identifier "general" 826 associated with a universally unique identifier 828, a descriptive identifier "hand and fingers" 830 associated with a universally unique identifier 832, a descriptive identifier "hip and pelvis" 834 associated with a universally unique identifier 836, a descriptive identifier "knee and thigh" 838 associated with a universally unique identifier 840, and a descriptive identifier "lower arm and wrist" 842 associated with a universally unique identifier 844.

While five (5) levels are illustrated in this disclosure, the system can include any number of levels, and each level can include any number of descriptive identifiers.

Figure 9:
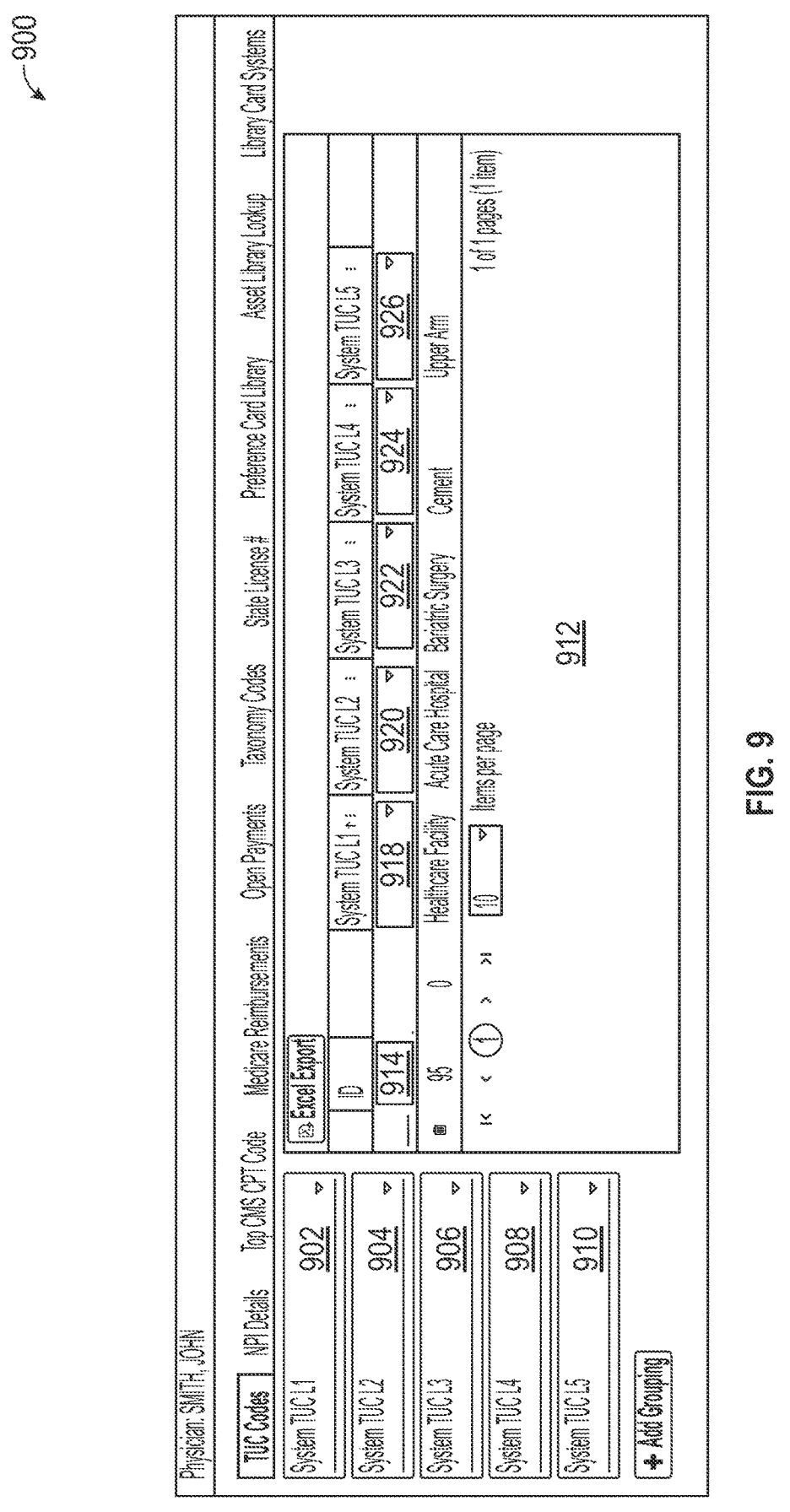

FIG. 9 is a sample graphical user interface 900 for assigning descriptive identifiers associated with universally unique identifiers to a data item, in accordance with an exemplary embodiment. The user interface 900 includes one or more options for selecting one or more descriptive identifiers to assign to the data item. In the exemplary embodiment, the data item is a physician. A user can assign the physician universally unique identifiers from levels 1-5, as described above in FIGS. 3-8, depending on information associated with the physician. For example, level 1 may be the medical type (e.g., physician), level 2 may be the specialty (e.g., cardiology), and so forth. These assignments may be based on data derived from different coding schemes.

In the exemplary embodiment, the user may assign a descriptive identifier for each level 1-5. Each level may include descriptive identifiers associated with a particular group, category, specialization, etc. For example, user interface 900 may include a drop down menu 902 to select available descriptive identifiers associated with level 1, a drop down menu 904 to select available descriptive identifiers associated with level 2, a drop down menu 906 to select available descriptive identifiers associated with level 3, a drop down menu 908 to select available descriptive identifiers associated with level 4, and a drop down menu 910 to select available descriptive identifiers associated with level 5. One or more of these descriptive identifiers may have been created using the graphical user interface 450 described in FIG. 4B for creating a descriptive identifier associated with a universally unique identifier.

The results of these selections are displayed graphically on the user interface 900 within section 912. Section 912 includes a column 914 for identification numbers associated with a set of descriptive identifiers assigned to the data item, a column 918 for a descriptive identifier assigned at level 1 (e.g., healthcare facility), a column 920 for a descriptive identifier assigned at level 2 (e.g., acute care hospital), a column 922 for a descriptive identifier assigned at level 3 (e.g., bariatric surgery), a column 924 for a descriptive identifier assigned at level 4 (e.g., cement), and a column 9926 for a descriptive identifier assigned at level 5 (e.g., upper arm). In some embodiments, one or more descriptive identifiers may not be assigned at the one or more levels. If a descriptive identifier is not assigned at a level, the associated level under column 918, 920, 922, 924, or 926 will be empty.

In some embodiments, the system may be fully automated, such that the system creates descriptive identifiers and associate each descriptive identifier with a universally unique identifier, obtains data from one or more data sources, parse out particular data items within the data (for example, using data recognition or word searching), and automatically assigns a descriptive identifiers to one or more data items based on the data items and the descriptive identifiers. In other embodiments, a user creates the descriptive identifiers (for example, using FIG. 4B), reviews the data from one or more data sources, identifies particular data items within the data (e.g., name of physicians), and assigns a universally unique identifier to each data item based on the data items, data obtained from the data sources, and the descriptive identifiers (for example, using FIG. 9).

In scenarios where a data item is already known/identified and stored in the system (e.g., a physician's name), in one embodiment, the system obtains data from one or more data sources, parse out particular data items within the data (for example, using data recognition or word searching), and automatically assigns descriptive identifiers to the known data item based on the data items and descriptive identifiers. In other embodiments, a user reviews the data from one or more data sources, identifies particular data items within the data, and assigns descriptive identifiers to the known data item based on the data items, data obtained from the data sources, and descriptive identifiers (for example, using FIG. 9). For example, in FIG. 9, the physician John Smith is already stored in the system, and the user may assign descriptive identifiers (e.g., "upper arm") to John Smith based on retrieved data (e.g., data shows John Smith performs upper arm surgeries).

FIGS. 10A-10B is a graphical user interface 1000 displaying descriptive identifiers associated with universally unique identifiers for a sample physician, in accordance with an exemplary embodiment. The user interface 1000 displays information associated with the physician that may include information obtained from one or more data sources with different schemes.

In the illustrated embodiment, the user interface 1000 includes a column 1002 for NPI numbers, a column 1004 for taxonomy codes, a column 1006 for taxonomy switches, a column 1008 for groupings, a column 1010 for classifications, and a column 1012 for specializations. This data may be obtained from a NPI registry database. As such, as illustrated, the physician is associated with a NPI number under column 1002, a taxonomy code under column 1004, a taxonomy switch under column 1006, a grouping under column 1008, a classification under column 1010, and a specialization under column 1012.

The user interface 1000 further includes a column 1014 for a level 1 descriptive identifier, a column 1016 for a level 2 descriptive identifier, a column 1018 for a level 3 descriptive identifier, a column 1020 for a level 4 descriptive identifier, and a column 1022 for a level 5 descriptive identifier. As such, as illustrated, physician "John Smith" is associated with a "physician" descriptive identifier under column 1014, a "family medicine" descriptive identifier under column 1016, a "bariatric surgery" descriptive identifier under column 1018, a "cement" descriptive identifier under column 1020, and a "upper arm" descriptive identifier under column 1022. These descriptive identifiers may be assigned to the physician based on data obtained from one or more data sources with different data schemes, and enables a user to identify that the physician is associated with the listed practices and surgeries.

In the illustrated example, the physician "John Smith" is the data item and the descriptive identifiers are assigned to this data item. However, in other embodiments, there may be a different data item, such as a hospital.

A user can select the pulldown option 1102 to select to view physicians associated with a particular universally unique identifier (for example, all physicians associated with pathology).

The user interface 1000 further includes a column 1024 for master universally unique identifiers. The system generates a master universally unique identifier based on the universally unique identifiers assigned to the physician. Accordingly, if two physicians have the same master universally unique identifier, the physicians also share the same universally unique identifiers.

FIG. 11 is a graphical user interface 1100 displaying sample physicians associated with descriptive identifiers, in accordance with an exemplary embodiment. The user interface 1100 includes physician data obtained from one or more data source, including a column 1102 for NPI numbers, a column 1104 for last names, a column 1106 for first names, a column 1108 for credentials, and a column 1110 for taxonomies. In addition, the graphical user interface 1100 includes a column 1112 for a first descriptive identifier and a column 1114 for a second descriptive identifier. Each physician is associated with an assigned descriptive identifier at a first level under column 1112 and an assigned descriptive identifier at a second level under column 1114. For example, user interface 1100 identifies physician John Smith as a physician (level 1) and specializing in internal medicine (level 2).

In some embodiments, a user can select the pulldown option 1102 to view physicians associated with a particular universally unique identifier (for example, all physicians associated with the descriptive identifier "pathology"). The system retrieves from a database all physicians associated with the universally unique identifier for "pathology".

FIGS. 12A-12B is a graphical user interface 1200 displaying sample facilities associated with descriptive identifiers, in accordance with an exemplary embodiment. The user interface 1200 includes facility data obtained from one or more data source, including a column 1202 for CCN identifiers 1202, a column 1204 for grandparent facility names, a column 1206 for parent facility names, and a column 1208 for child count. In addition, each facility is assigned a descriptive identifier at one or more levels, as described above, depending on the facility's type, specialty, etc. In the illustrated embodiment, the graphical user interface 1200 includes a column 1210 for descriptive identifiers assigned to the facilities at a first level, a column 1212 for descriptive identifiers assigned to the facilities at a second level, a column 1214 for descriptive identifiers assigned to the facilities at a third level, a column 1216 for descriptive identifiers assigned to the facilities at a fourth level, and a column 1218 for descriptive identifiers assigned to the facilities at a fifth level. Each facility is associated with an assigned descriptive identifiers at a first level, an assigned descriptive identifiers at a second level, an assigned descriptive identifiers at a third level, an assigned descriptive identifiers at a fourth level, and/or an assigned descriptive identifiers at a fifth level. For example, user interface 1200 identifies the facility "Hartford Healthcare" as a healthcare facility (level 1), an acute care hospital (level 2), performs bariatric surgery (level 3), procedures associated with cement (level 4), and procedures associated with the upper arm (level 5). These assignments may be based on data obtained from two or more data sources with different data schemes.

In some embodiments, the user can select the pulldown option 1202 to view facilities associated with a particular universally unique identifier (for example, all facilities associated with "bariatric surgery").

The user interface 1000 further includes a column 1220 for master universally unique identifiers. The system generate a master universally unique identifier for each facility based on the universally unique identifiers assigned to the facility. Accordingly, if two facilities have the same master universally unique identifier, the facilities also share the same universally unique identifiers.

FIGS. 13A-13E displays the data linage 1300 through the implemented data layers in the technology stack of the system, in accordance with an exemplary embodiment. Columns from left to right include the UI Layer 1304 (contains 'Screen Schema' Label), Middleware Layer 1306 and 1308 (columns 2 and 3 from the left, contains 'DB Name' Label), and Original Data Source 1301, 1312, 1314, 1316 (rightmost column: contains 'CMS MEDICARE PROVIDER UTILIZATION AND PAYMENT DATA: PHYSICIAN'.)

FIGS. 14A-14B illustrates a user interface 1400 displaying an information index for a sample physician, in accordance with an exemplary embodiment. The user interface 1400 displays information retrieved from one or more data sources with different schemes.

In an exemplary embodiment, the user interface 1400 displays descriptive identifiers 1402 associated with data retrieved from the NPI data registry. The system (e.g., the Indexing Engine) or a user creates descriptive identifiers appropriate for the NPI data registry. The system (e.g., the Indexing Engine) generates universally unique identifiers for the descriptive identifiers. The system (e.g., the Data-Retrieving Engine) harvests and/or retrieves data from the NPI data registry. In some embodiments, the system (e.g., the Indexing Engine) parses the data retrieved from the NPI data registry to identify data items associated with the sample physician. The system (e.g., the Indexing Engine) or a user assigns descriptive identifiers to the sample physician based on the data retrieved from the NPI data registry. The user interface 1400 displays the descriptive identifiers 1402 assigned to the sample physician based on the data retrieved from the NPI data registry. In the exemplary embodiment, the universally unique identifiers are assigned from levels 1-5; however, more of less levels may be used in other embodiments.

In an exemplary embodiment, the user interface 1400 further displays descriptive identifiers 1404 associated with data retrieved from the NPPES data registry. The system (e.g., the Indexing Engine) or a user creates descriptive identifiers appropriate for the NPPES data registry. The system (e.g., the Indexing Engine) generates universally unique identifiers for the descriptive identifiers. The system (e.g., the Data-Retrieving Engine) harvests and/or retrieves data from the NPPES data registry. In some embodiments, the system (e.g., the Indexing Engine) parses the data retrieved from the NPPES data registry to identify data items. The system (e.g., the Indexing Engine) or a user assigns descriptive identifiers to the sample physician based on the data retrieved from the NPPES data registry. The user interface 1400 displays the descriptive identifiers 1404 assigned to the sample physician based on the data retrieved from the NPPES data registry. In the exemplary embodiment, the universally unique identifiers are assigned from levels 1-5; however, more or less levels may be used in other embodiments.

In an exemplary embodiment, the user interface 1400 displays descriptive identifiers 1406 associated with data retrieved from the CPT data registry. The system (e.g., the Indexing Engine) or a user creates descriptive identifiers appropriate for the CPT data registry. The system (e.g., the Indexing Engine) generates universally unique identifiers for the descriptive identifiers. The system (e.g., the Data-Retrieving Engine) harvests and/or retrieves data from the CPT data registry. In some embodiments, the system (e.g., the Indexing Engine) parses the data retrieved from the CPT data registry to identify data items. The system (e.g., the Indexing Engine) or a user assigns descriptive identifiers to the sample physician based on the data retrieved from the CPT data registry. The user interface 1400 displays the descriptive identifiers assigned to the sample physician based on the data retrieved from the CPT data registry. In the exemplary embodiment, the universally unique identifiers are assigned from levels 1-5; however, more of less levels may be used in other embodiments.

In the exemplary embodiment, the user interface 1400 further displays physician information, such as name, address, NPI number, taxonomy, etc., obtained from the NPI data registry, the NPPES data registry, and/or the CPT data registry.

Figure 15:
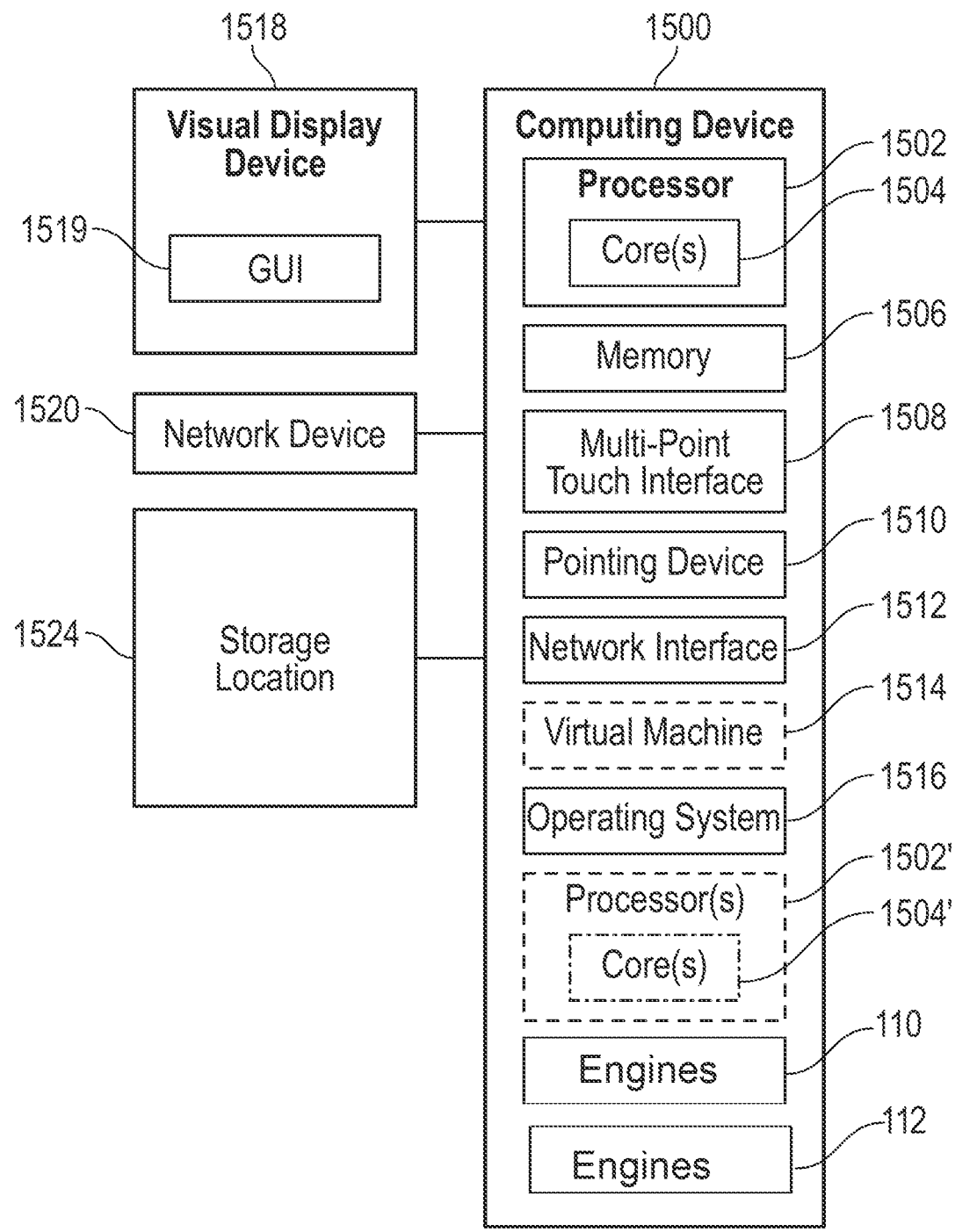
FIG. 15 is a block diagram of an exemplary computing device that can be used to perform one or more steps of the methods provided by exemplary embodiments.

FIG. 15 is a block diagram of an exemplary computing device 1500 that can be used to perform one or more steps of the methods provided by exemplary embodiments. In an exemplary embodiment, computing device 1500 is a computing system (i.e., computing device 102) and/or a user device (i.e., client device 104). Computing device 1500 includes one or more non-transitory computer-readable media for storing one or more computer-executable instructions or software for implementing exemplary embodiments. The non-transitory computer-readable media can include, but are not limited to, one or more varieties of hardware memory, non-transitory tangible media (for example, one or more magnetic storage disks, one or more optical disks, one or more USB flashdrives), and the like. For example, a memory 1506 included in computing device 1500 can store computer-readable and computer-executable instructions or software for implementing exemplary embodiments. Computing device 1500 also includes a processor 1502 and an associated core 1504, and optionally, one or more additional processor(s) 1502' and associated core(s) 1504' (for example, in the case of computer systems having multiple processors/cores), for executing computer-readable and computer-executable instructions or software stored in memory 1506 and other programs for controlling system hardware. Processor 1502 and processor(s) 1502' can each be a single core processor or multiple core (1504 and 1504') processor. Computing device 1500 may also include the Indexing Engine 110 and a Data-Retrieving Engine 112.

In some embodiments, computing device 1500 may include a browser application. As described above, browser application can enable a user to view the user interfaces as described herein.

Virtualization can be employed in computing device 1500 so that infrastructure and resources in the computing device can be shared dynamically. A virtual machine 1514 can be provided to handle a process running on multiple processors so that the process appears to be using only one computing resource rather than multiple computing resources. Multiple virtual machines can also be used with one processor.

Memory 1506 can include a computer system memory or random access memory, such as DRAM, SRAM, EDO RAM, and the like. Memory 1506 can include other varieties of memory as well, or combinations thereof. In some embodiments, a user can interact with computing device 1500 through a visual display device 1518, such as a touch screen display or computer monitor, which can display one or more user interfaces 1519 that can be provided in accordance with exemplary embodiments, for example, the exemplary user interfaces. Visual display device 1518 may also display other aspects, elements and/or information or data associated with exemplary embodiments. Computing device 1500 may include other I/O devices for receiving input from a user, for example, a keyboard or any suitable multi-point touch interface 1508, a pointing device 1510 (e.g., a pen, stylus, mouse, or trackpad). The keyboard 1508 and pointing device 1510 may be coupled to visual display device 1518. Computing device 1500 may include other suitable conventional I/O peripherals.

Computing device 1500 can also include one or more storage devices 1524, such as a hard-drive, CD-ROM, or other computer readable media, for storing data and computer-readable instructions and/or software, that implements embodiments of the described system, as described herein, or portions thereof. Exemplary storage device 1524 can also store one or more storage devices for storing any suitable information required to implement exemplary embodiments.

Computing device 1500 can include a network interface 1512 configured to interface via one or more network devices 1522 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 1512 can include a built-in network adapter, network interface card, PCMCIA network card, card bus network adapter, wireless network adapter, USB network adapter, modem or any other device suitable for interfacing computing device 1500 to any variety of network capable of communication and performing the operations described herein. Moreover, computing device 1500 can be any computer system, such as a workstation, desktop computer, server, laptop, handheld computer, tablet computer (e.g., the iPad® tablet computer), mobile computing or communication device (e.g., the iPhone® communication device), or other form of computing or telecommunications device that is capable of communication and that has sufficient processor power and memory capacity to perform the operations described herein.

Computing device 1500 can run any operating system 1516, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, any operating systems for mobile computing devices, or any other operating system capable of running on the computing device and performing the operations described herein. In exemplary embodiments, the operating system 1516 can be run in native mode or emulated mode. In an exemplary embodiment, the operating system 1516 can be run on one or more cloud machine instances.

Figure 16:
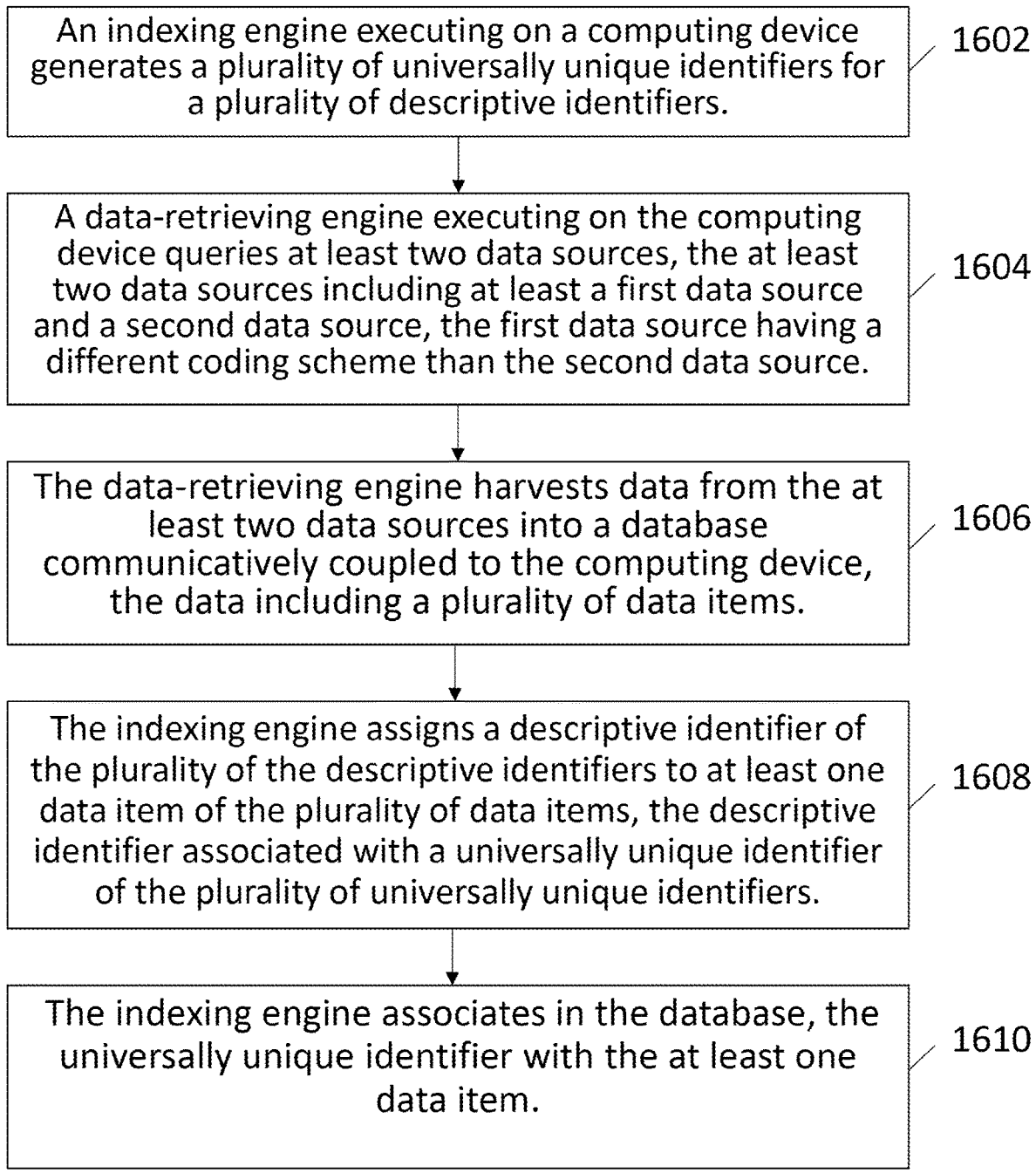
FIG. 16 is a flowchart illustrating an exemplary method for a universal indexing scheme for indexing data, in accordance with an exemplary embodiment.

FIG. 16 is a flowchart illustrating an exemplary method for a universal indexing scheme for indexing data, in accordance with an exemplary embodiment. At step 1602, an indexing engine executing on a computing device generates a plurality of universally unique identifiers for a plurality of descriptive identifiers. At step 1604, a data-retrieving engine executing on the computing device queries at least two data sources, the at least two data sources including at least a first data source and a second data source, the first data source having a different coding scheme than the second data source. At step 1606, the data-retrieving engine harvests data from the at least two data sources into a database communicatively coupled to the computing device, the data including a plurality of data items. At step 1608, the indexing engine assigns a descriptive identifier of the plurality of the descriptive identifiers to at least one data item of the plurality of data items, the descriptive identifier associated with a universally unique identifier of the plurality of universally unique identifiers. At step 1610, the indexing engine associates in the database, the universally unique identifier with the at least one data item.

The following description is presented to enable any person skilled in the art to create and use a computer system configuration and related method and systems, as taught herein. Various modifications to the exemplary embodiments will be readily apparent to those skilled in the art, and the generic principles defined herein may be applied to other embodiments and applications without departing from the spirit and scope of the disclosure. Moreover, in the following description, numerous details are set forth for the purpose of explanation. However, one of ordinary skill in the art will realize that the disclosure may be practiced without the use of these specific details. In other instances, well-known structures and processes are shown in block diagram form in order not to obscure the description of the disclosure with unnecessary detail. Thus, the present disclosure is not intended to be limited to the embodiments shown, but is to be accorded the widest scope consistent with the principles and features disclosed herein.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements, device components or method steps, those elements, components or steps can be replaced with a single element, component or step. Likewise, a single element, component or step can be replaced with a plurality of elements, components or steps that serve the same purpose. Moreover, while exemplary embodiments have been shown and described with references to particular embodiments thereof, those of ordinary skill in the art will understand that various substitutions and alterations in form and detail can be made therein without departing from the scope of the disclosure. Further still, other aspects, functions and advantages are also within the scope of the disclosure.

Exemplary flowcharts are provided herein for illustrative purposes and are non-limiting examples of methods. One of ordinary skill in the art will recognize that exemplary methods can include more or fewer steps than those illustrated in the exemplary flowcharts, and that the steps in the exemplary flowcharts can be performed in a different order than the order shown in the illustrative flowcharts.

We claim:

1. A method for a universal indexing scheme for indexing data, the method comprising:

generating, via an indexing engine executing on a computing device, a plurality of universally unique identifiers for a plurality of descriptive identifiers;

querying, via a data-retrieving engine executing on the computing device, at least two data sources, the at least two data sources including at least a first data source and a second data source, the first data source having a different coding scheme than the second data source;

harvesting, via the data-retrieving engine, data from the at least two data sources into a database communicatively coupled to the computing device, the data including a plurality of data items;

assigning, via the indexing engine, a first descriptive identifier of the plurality of the descriptive identifiers to a first data item of the plurality of data items, the first descriptive identifier associated with a universally unique identifier of the plurality of universally unique identifiers and where the first data item is obtained from the first data source and is associated with a first coding scheme;

assigning, via the indexing engine, the first descriptive identifier to a second data item, where the second data item is obtained from the second data source and is associated with a second coding scheme that is different from the first coding scheme; and associating, via the indexing engine, in the database, an universally unique identifier from the plurality of universally unique identifiers with the first data item and the second data item.

2. The method of claim 1, wherein the plurality of data items include at least one of physician names, hospital names, taxonomies, classifications, specializations, and medical procedures.

3. The method of claim 1, further comprising:
receiving, via a user interface, a selection of a first descriptive identifier associated with a first universally unique identifier of the plurality of universally unique identifiers;
retrieving one or more data items associated with the first universally unique identifier;
displaying, on the user interface, the one or more data items associated with the first universally unique identifier.

4. The method of claim 1, further comprising:
displaying, on a user interface, the plurality of descriptive identifiers and the plurality of universally unique identifiers.

5. The method of claim 1, further comprising generating a universally unique identifier for a combination of descriptive identifiers that uniquely identifies the combination of descriptive identifiers.

6. A system for a universal indexing scheme for indexing data, the system comprising:
at least one computing device executing an data-retrieving engine and an indexing engine, the at least one computing device communicatively coupled to a database, the data-retrieving engine configured to:
query at least two data sources, the at least two data sources including at least a first data source and a second data source, the first data source having a different coding scheme than the second data source, and
harvest data from the at least two data sources into the database communicatively coupled to the computing device, the data including a plurality of data items; and
the indexing engine configured to:
generate a plurality of universally unique identifiers for a plurality of descriptive identifiers,
assign a first descriptive identifier of the plurality of the descriptive identifiers to a first data item of the plurality of data items, the first descriptive identifier associated with a universally unique identifier of the plurality of universally unique identifiers and where the first data item is obtained from the first data source and is associated with a first coding scheme, and
assign the first descriptive identifier to a second data item, where the second data item is obtained from the second data source and is associated with a second coding scheme that is different from the first coding scheme; and associate in the database, an universally unique identifier from the plurality of universally unique identifiers with the first data item and the second data item.

7. The system of claim 6, wherein the plurality of data items include at least one of physician names, hospital names, taxonomies, classifications, specializations, and medical procedures.

8. The system of claim 6, further comprising:
a user interface communicatively coupled to the computing device, the user interface configured to:
receive a selection of a first descriptive identifier associated with a first universally unique identifier of the plurality of universally unique identifiers; and
display the one or more data items associated with the first universally unique identifier.

9. The system of claim 6, further comprising:
a user interface communicatively coupled to the computing device, the user interface configured to display the plurality of descriptive identifiers and the plurality of universally unique identifiers.

10. The system of claim 6, the indexing engine further configured to generate a universally unique identifier for a combination of descriptive identifiers that uniquely identifies the combination of descriptive identifiers.

11. A non-transitory computer readable medium comprising instructions that when executed cause a computing device to:
generate, via an indexing engine executing on the computing device, a plurality of universally unique identifiers for a plurality of descriptive identifiers;
query, via a data-retrieving engine executing on the computing device, at least two data sources, the at least two data sources including at least a first data source and a second data source, the first data source having a different coding scheme than the second data source;
harvest, via the data-retrieving engine, data from the at least two data sources into a database communicatively coupled to the computing device, the data including a plurality of data items;
assign, via the indexing engine, a first descriptive identifier of the plurality of the descriptive identifiers to a first data item of the plurality of data items, the first descriptive identifier associated with a universally unique identifier of the plurality of universally unique identifiers and where the first data item is obtained from the first data source and is associated with a first coding scheme;
assign, via the indexing engine, the first descriptive identifier to a second data item, where the second data item is obtained from the second data source and is associated with a second coding scheme that is different from the first coding scheme; and
associate, via the indexing engine, in the database, an universally unique identifier from the plurality of universally unique identifiers with the first data item and the second data item.

12. The non-transitory computer readable medium of claim 11, wherein the plurality of data items include at least one of physician names, hospital names, taxonomies, classifications, specializations, and medical procedures.

13. The non-transitory computer readable medium of claim 11, wherein execution of the instructions further causes the computing device to:

receive, via a user interface, a selection of a first descriptive identifier associated with a first universally unique identifier of the plurality of universally unique identifiers;

retrieve one or more data items associated with the first universally unique identifier;

display, on the user interface, the one or more data items associated with the first universally unique identifier.

14. The non-transitory computer readable medium of claim 11, wherein execution of the instructions further causes the computing device to:

display, on a user interface, the plurality of descriptive identifiers and the plurality of universally unique identifiers.

* * * * *